(12) United States Patent
Alford et al.

(10) Patent No.: US 10,663,548 B2
(45) Date of Patent: *May 26, 2020

(54) SYSTEM AND METHOD FOR MAGNETIC RESONANCE IMAGING

(71) Applicant: The University of Western Ontario, London (CA)

(72) Inventors: Jamu Alford, London (CA); Blaine Chronik, London (CA); Timothy Scholl, London (CA)

(73) Assignee: THE UNIVERSITY OF WESTERN ONTARIO, London (CA)

( * ) Notice: Subject to any disclaimer, the term of this patent is extended or adjusted under 35 U.S.C. 154(b) by 1005 days.

This patent is subject to a terminal disclaimer.

(21) Appl. No.: 15/166,711

(22) Filed: May 27, 2016

(65) Prior Publication Data
US 2016/0274208 A1 Sep. 22, 2016

Related U.S. Application Data

(63) Continuation of application No. 13/126,253, filed as application No. PCT/CA2009/001538 on Oct. 27, 2009, now Pat. No. 9,423,480.
(Continued)

(51) Int. Cl.
| | | |
|---|---|---|
| *G01R 33/56* | (2006.01) | |
| *A61K 49/10* | (2006.01) | |
| *G01R 33/44* | (2006.01) | |
| *G01R 33/561* | (2006.01) | |
| *G01R 33/381* | (2006.01) | |
| *G01R 33/385* | (2006.01) | |
| *G01R 33/50* | (2006.01) | |
| *G10K 9/00* | (2006.01) | |

(52) U.S. Cl.
CPC ........ *G01R 33/5601* (2013.01); *A61K 49/103* (2013.01); *G01R 33/381* (2013.01); *G01R 33/385* (2013.01); *G01R 33/445* (2013.01); *G01R 33/5608* (2013.01); *G01R 33/5617* (2013.01); *G01R 33/44* (2013.01); *G01R 33/50* (2013.01); *G01R 33/56* (2013.01); *G10K 9/00* (2013.01)

(58) Field of Classification Search
CPC ........................... A61K 49/06; G01R 33/5601
USPC ....................... 600/410, 420, 431
See application file for complete search history.

(56) References Cited

U.S. PATENT DOCUMENTS

| | | |
|---|---|---|
| 4,577,152 A | 3/1986 | Macovski |
| 4,656,425 A | 4/1987 | Bendel |

(Continued)

FOREIGN PATENT DOCUMENTS

WO  2004019996 A1  3/2004

OTHER PUBLICATIONS

Ungersma [Magnetic Resonance Imaging with T1 Dispersion Contrast Magnetic Resonance in Medicine 55:1362-1371 (2006)]. (Year: 2006).*

(Continued)

*Primary Examiner* — Oommen Jacob
(74) *Attorney, Agent, or Firm* — Perry + Currier

(57) ABSTRACT

A method for contrast agent enhanced magnetic resonance imaging (MRI) of a target sample, comprising generating a magnetic field shift in a polarizing magnetic field during a relaxation portion of an MRI pulse sequence and thereafter acquiring an MR image.

7 Claims, 19 Drawing Sheets

Related U.S. Application Data

(60) Provisional application No. 61/108,734, filed on Oct. 27, 2008.

(56) References Cited

U.S. PATENT DOCUMENTS

| | | | |
|---|---|---|---|
| 4,718,424 A * | 1/1988 | Nishimura | G01R 33/56308 324/306 |
| 4,727,326 A | 2/1988 | Kaplan et al. | |
| 4,748,409 A | 5/1988 | Frahm et al. | |
| 5,063,348 A * | 11/1991 | Kuhara | G01R 33/3607 324/307 |
| 5,144,328 A | 9/1992 | Blake et al. | |
| 5,304,931 A * | 4/1994 | Flamig | G01R 33/446 324/309 |
| 5,335,660 A * | 8/1994 | Dumoulin | G01R 33/50 600/419 |
| 5,363,042 A | 11/1994 | Dumoulin | |
| 5,450,010 A * | 9/1995 | Van Der Meulen | G01R 33/56518 324/309 |
| 5,459,401 A * | 10/1995 | Kiefer | G01R 33/561 324/307 |
| 5,509,412 A * | 4/1996 | Bahn | A61B 5/055 324/306 |
| 5,565,777 A * | 10/1996 | Kanayama | G01R 33/465 324/309 |
| 5,578,922 A | 11/1996 | Lurie et al. | |
| 5,684,400 A * | 11/1997 | Tsukamoto | G01R 33/561 324/307 |
| 5,729,139 A * | 3/1998 | Goto | G01R 33/56518 324/309 |
| 6,317,620 B1 * | 11/2001 | Ho | G01R 33/56308 324/306 |
| 6,389,304 B1 * | 5/2002 | Van Den Brink | G01R 33/56341 324/306 |
| 6,459,922 B1 | 10/2002 | Zhang | |
| 6,603,989 B1 * | 8/2003 | Yablonskiy | G01R 33/50 600/410 |
| 6,662,038 B2 | 12/2003 | Prince | |
| 6,794,869 B2 | 9/2004 | Brittain | |
| 6,801,034 B2 | 10/2004 | Brittain et al. | |
| 6,861,045 B1 * | 3/2005 | Lauffer | A61K 49/0052 424/9.364 |
| 6,870,367 B2 | 3/2005 | Kirsch | |
| 6,963,766 B2 | 11/2005 | Ho et al. | |
| 7,251,519 B2 * | 7/2007 | Axelsson | G01R 33/5601 324/307 |
| 7,403,810 B2 | 7/2008 | Li et al. | |
| 7,519,412 B2 | 4/2009 | Mistretta | |
| 7,835,783 B1 | 11/2010 | Aletras | |
| 8,334,697 B2 | 12/2012 | Overweg et al. | |
| 10,054,650 B2 * | 8/2018 | Alford | G01R 33/445 |
| 2003/0185760 A1 * | 10/2003 | Lanza | A61K 49/1881 424/9.321 |
| 2004/0162483 A1 * | 8/2004 | Kimura | G01R 33/56308 600/419 |
| 2005/0007111 A1 * | 1/2005 | Frydman | G01N 24/08 324/307 |
| 2005/0261575 A1 | 11/2005 | Conolly et al. | |
| 2007/0299335 A1 * | 12/2007 | Declerck | A61B 5/055 600/420 |
| 2008/0167549 A1 | 7/2008 | Balaban et al. | |
| 2009/0179643 A1 * | 7/2009 | Lin | G01R 33/34084 324/312 |
| 2009/0253983 A1 | 10/2009 | Foo et al. | |
| 2010/0060282 A1 * | 3/2010 | Shvartsman | G01R 33/385 324/318 |
| 2013/0021030 A1 | 1/2013 | Zuehlsdorff et al. | |
| 2015/0293193 A1 * | 10/2015 | Alford | G01R 33/445 324/309 |
| 2016/0274208 A1 * | 9/2016 | Alford | A61K 49/103 |

OTHER PUBLICATIONS

S.E. Ungersma et al., "Contrast-Enhanced MRI with Fat Suppression using T1Disperson" Proc. Intl. Soc. Mag. Reason, Med. 14 (2009), 1 page (1696).

D.J. Lurie "Quadrpole-Dips Measured by Whole-Body Field-Cycling Relaxometry and Imaging," University of Aberdeen, Department of Bio-Medical Physics and Bio-Engineering, 1 page, no date available.

G.R. Davis et al., "Quantitative Field-Cycling T1 Dispersion Imaging," Proc. Intl. Mag. Reson. Med. 13 (2005), p. (2187).

J. Alford et al., "Developement of a Simulation Tool for Field Cycled MRT," Proc. Intl. Soc. Med. Reson. Med. 13 (2005), 1 page (867).

S. Ungersma et al., "In Vivo MRI Imaging with T1 Dispersion Contrast," Proc. Intl. Soc. Med.13 (2005) 1 page (414).

Matter, Nathaniel et al., "Rapid polarizing field cycling in magnetic resonance imaging," Medical Imaging, IEEE Transactions on Jan. 25, 2006, pp. 84-93.

Gilbert et al., "Design of Field Cycled Magnetic Resonance Systems for Small Animal Imaging," Physics in Medicine and Biology 51:2823-2841 (2006).

Ugerasma et al. "Magnetic Resonance Imaging with T1 Dispersion Contrast," Magnetic Resonance in Medicine 55:1362-1371 (2006) (Abstract Only).

Eldredge et al., "Species Dependence on Plasma Protein Binding and Relaxivity of the Gadolinium-Based MRI Contrast Agent MS-325," Investigative Radiology 41:229-243 (2006) (Abstract Only).

Canadian Office Action for Application No. 2717906, dated Aug. 27, 2015, pp. 1-4.

* cited by examiner

SYSTEM AND METHOD FOR MAGNETIC RESONANCE IMAGING

CROSS-REFERENCE TO RELATED APPLICATIONS

This application claims the benefit of U.S. Provisional Application No. 61/108,734 to Alford et al. filed on Oct. 27, 2008 entitled "System and Method for Magnetic Resonance Imaging", the content of which is incorporated herein by reference.

FIELD OF THE INVENTION

This specification relates generally to magnetic resonance imaging and more particularly, to a system and method for producing image contrast in magnetic resonance imaging.

BACKGROUND OF THE INVENTION

Molecular imaging is the in vivo study and measurement of biological processes at the molecular level (1). Nuclear Magnetic Resonance (NMR) Imaging, or Magnetic Resonance Imaging (MRI) as it is commonly known, is a non-invasive imaging modality that can produce high resolution, high contrast images of the interior of a subject. MRI involves the interrogation of the nuclear magnetic moments of a sample placed in a strong magnetic field with radio frequency (RF) magnetic fields. During MRI the subject, typically a human patient, is placed into the bore of an MRI machine and is subjected to a uniform magnetic field $B_0$ produced by a polarizing magnet housed within the MRI machine. Radio frequency (RF) pulses, generated by RF coils housed within the MRI machine in accordance with a particular localization method, are typically used to scan target tissue of the patient. MRI signals are radiated by excited nuclei in the target tissue in the intervals between consecutive RF pulses and are sensed by the RF coils. During MRI signal sensing, gradient magnetic fields are switched rapidly to alter the uniform magnetic field at localized areas thereby allowing spatial localization of MRI signals radiated by selected slices of the target tissue. The sensed MRI signals are in turn digitized and processed to reconstruct images of the target tissue slices using one of many known techniques.

When a target substance, such as human tissue, is subjected to the static polarizing magnetic field $B_0$, the individual magnetic moments of the spins in the tissue attempt to align with the static polarizing magnetic field $B_0$, but precess about the static polarizing magnetic field $B_0$ in random order at their characteristic Larmor frequency. The net magnetization vector lies along the direction of the static polarizing magnetic field $B_0$ and is referred to as the equilibrium magnetization $M_0$. In this configuration, the Z component of the magnetization or longitudinal magnetization $M_Z$ is equal to the equilibrium magnetization $M_0$. If the target tissue is subjected to an excitation magnetic field $B_1$, which is in the x-y plane and which is near the Larmor frequency, the longitudinal magnetization $M_Z$ may be rotated, or "tipped" into the x-y plane to produce a net transverse magnetic moment $M_{XY}$. When the excitation magnetic field $B_1$ is terminated, relaxation of the excited spins occurs, with a signal being emitted that effects the magnitude of radiated MRI signals. The emitted signal is received and processed to form an image.

In particular, when the excitation magnetic field $B_1$ is terminated, the longitudinal magnetization $M_Z$ relaxes back to its equilibrium. The time constant that describes how the longitudinal magnetization $M_Z$ returns to its equilibrium value is commonly referred to as the spin lattice relaxation time $T_1$. The spin lattice relaxation time $T_1$ characterizes the time required to reduce the difference between the longitudinal magnetization $M_Z$ and its equilibrium longitudinal magnetization value $M_0$ to zero.

The net transverse magnetic moment $M_{XY}$ also relaxes back to its equilibrium when the excitation magnetic field $B_1$ is terminated. The time constant that describes how the transverse magnetic moment $M_{XY}$ returns to its equilibrium value is commonly referred to as transverse relaxation time or spin-spin relaxation time $T_2$. The transverse relaxation time $T_2$ characterizes the time required to reduce the transverse magnetic moment $M_{XY}$ to zero. Both the spin lattice relaxation time $T_1$ and the transverse relaxation time $T_2$ are tissue specific and vary with concentration of different chemical substances in the tissue as well as with different microstructural features of the tissue. Variations of the spin lattice relaxation time $T_1$ and/or the transverse relaxation time $T_2$ from normal can also be indicative of disease or injury.

Like many diagnostic imaging modalities, MRI can be used to differentiate tissue types, e.g. muscles from tendons, white matter from gray matter, healthy tissue from pathologic tissue, etc. There exist many different MRI techniques, the utility of each depending on the particular tissues under examination. Some techniques examine the rate of tissue magnetization, while others measure the amount of bound water or the velocity of blood flow. Often, several MRI techniques are used together to improve tissue identification. In general, the greater the number of identification methods available the better chance of identifying a certain tissue type or pathology.

In some instances, contrast agents or contrast materials may be used to emphasize certain anatomical regions. For example, a Gadolinium chelate injected into a blood vessel will produce enhancement of the vascular system, or the presence and distribution of leaky blood vessels. Iron-loaded stem cells, injected into the body and detected by MRI, will allow stem cell migration and implantation in vivo to be tracked.

Contrast agents can enhance imaging of target sites or tissues through the complementary processes of accumulation and activation. Accumulation occurs when the local concentration of the contrast agent is increased through metabolic uptake or molecular adhesion leading to localized image enhancement. A growing number of contrast agents are also activatable, their behavior mediated by interaction with a target molecule, such as a specific protein or macromolecule. Contrast agents demonstrating activation are interchangeably called "sensing", "smart", or "activatable" contrast agents.

Activatable contrast agents are used in MRI studies to improve the specificity of the contrast agent (2). Ideally activatable contrast agents produce no image enhancement in the inactivated state; however, to date, these contrast agents combined with conventional MRI have shown image intensity enhancement in both inactivated and activated states, with relatively modest signal intensity ratios between these two states.

Accordingly, there is a continuing need for improvements in MRI. It is therefore an object of an aspect to provide a novel system and method for producing image contrast in magnetic resonance imaging.

SUMMARY OF THE INVENTION

Accordingly, in one aspect there is provided a method for contrast agent enhanced magnetic resonance imaging (MRI)

of a target sample, comprising generating a magnetic field shift in a polarizing magnetic field during a relaxation portion of an MRI pulse sequence and thereafter acquiring an MR image.

In another aspect, there is provided a method of magnetic resonance imaging comprising subjecting a sample to polarizing magnetic fields of different strengths and acquiring a scan associated with each polarizing magnetic field; and processing the scans to generate selective image contrast of said sample based on the variation of at least one MR property of the sample in response to the different polarizing magnetic field strengths.

In yet another aspect, there is provided a magnetic resonance imaging method comprising performing multiple scans of a subject and generating an image for each scan, each scan being conducted utilizing a different polarizing magnetic field; and processing the images to yield an enhanced contrast image, wherein said performing comprises: shifting the polarizing magnetic field of an MRI machine in one direction during a relaxation portion of a first pulse sequence and thereafter acquiring an image; and shifting the polarizing magnetic field of the MRI machine in an opposite direction during a relaxation portion of a second pulse sequence and thereafter acquiring an image.

In still another aspect, there is provided an MRI machine comprising a housing having a bore in which a subject to be imaged is placed; a polarizing electromagnet accommodated by said housing and generating a generally uniform polarizing magnetic field within said bore; pulse generating coils to generate pulses in a sequence to scan the subject; and gradient coils to encode acquired MRI signals, wherein said gradient coils are further configured to generate a shift in the polarizing magnetic field during a relaxation portion of the sequence.

BRIEF DESCRIPTION OF THE DRAWINGS

Embodiments will now be described, by way of example only, with reference to the accompanying drawings in which.

DETAILED DESCRIPTION

Figure 1:
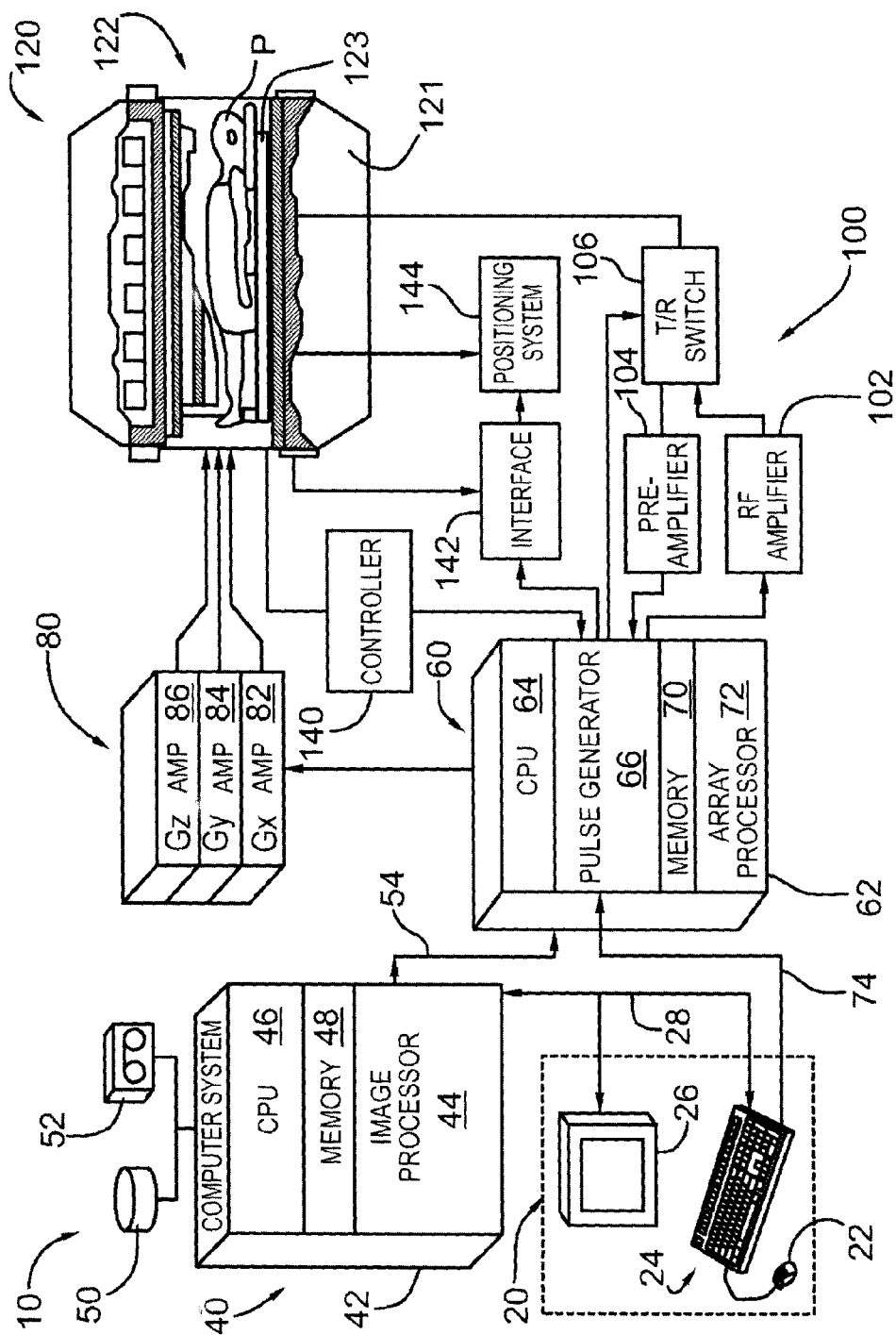
FIG. 1 is a schematic block diagram of an MRI system.

Embodiments described in the present specification relate to a method and system for magnetic resonance imaging of samples which make use of a dynamically controlled MRI polarizing magnetic field and a contrast agent or endogenous substance that demonstrates a magnetic field-dependent variation in one or more MRI properties. The system and method described herein provide increased specificity in MRI by utilizing an auxiliary magnetic field to modify the strength of the main polarizing magnetic field as a function of time during a relaxation portion of an MRI pulse sequence.

In one embodiment, an auxiliary magnetic field ΔB is applied during a relaxation portion of an MRI pulse sequence. More specifically, during the relaxation portion of the MRI pulse sequence the static magnetic field strength $B_0$ generated by the polarizing magnet of an MRI machine is either increased or decreased by an amount ΔB. The auxiliary magnetic field may be applied during part, substantially all, or all of the relaxation portion of the MRI pulse sequence.

Various examples of generating and applying the magnetic field ΔB are described herein. In one embodiment, an electromagnetic coil insert (ΔB insert) is incorporated into a conventional MRI machine, to generate a substantially uniform magnetic field, across an imaging region, during a relaxation portion of an MRI pulse sequence. In another embodiment, a gradient coil in a conventional MRI machine is programmed to generate a varying magnetic field, across an imaging region, during a relaxation portion of the MRI pulse sequence, with the target sample being placed offset from the iso-center of the MRI machine. In still another embodiment, a gradient coil is modified to generate a substantially uniform magnetic field, across an imaging region, during a relaxation portion of the MRI pulse sequence.

"Iso-center" refers to a location within an MRI machine where a varying magnetic field generated by a gradient coil is zero. Thus, in embodiments where a gradient coil induced linearly varying magnetic field is produced during a relaxation portion of the MRI pulse sequence, offsetting the target sample from the iso-center allows for the gradient coil induced magnetic field to be non-zero across the target sample. The iso-center typically coincides with the spatial center of a magnet assembly in an MRI machine.

"Relaxation" refers to a return of excited spins to their equilibrium distribution in which there is no transverse magnetization and/or the longitudinal magnetization is at its maximum value and oriented in the direction of the main static magnetic field $B_0$ generated by the MRI machine. After excitation the transverse magnetization decays toward zero with a characteristic time constant $T_2$, and the longitudinal magnetization returns toward equilibrium with a characteristic time constant $T_1$. The method and system take advantage of the change in longitudinal relaxivity vs. magnetic field strength, i.e. the relaxivity slope, to produce selective image contrast when a contrast agent binds to a given target molecule.

Turning now to FIG. 1, an MRI system is shown and is generally identified by reference numeral 10. The MRI system 10 comprises an operator console 20, a computer system 40, a system controller 60, a gradient amplifier system 80, an RF coil control circuit 100 and an MRI machine 120. The operator console 20 allows an operator to control the MRI system 10 including the production and display of images. The computer system 40 is responsive to commands generated by the operator console 120 and generates images for display. The system controller 60 communicates with the operator console 20, the computer system 40, the gradient amplifier system 80 and the RF coil control circuit 100 and orchestrates the acquisition of images in response to commands generated by the operator console 20. The MRI machine 120 communicates with the gradient amplifier system 80 and the RF coil control circuit 100.

The operator console 20 comprises an input device 22, a control panel 24 coupled to the input device 22, and a display 26. The input device 22 can comprise a mouse, joystick, keyboard, trackball, touch screen, light wand, voice control, or similar such device, and may be used for interactive geometry prescription. The operator console 20 communicates with the computer system 40 over a data communications link 28 thereby to enable an operator to control the production and presentation of images on the display 26.

The computer system 40 comprises a number of modules, which communicate with each other through a backplane 42. As can be seen, the modules of computer system 40 comprise an image processor module 44, a CPU module 46, and a memory buffer 48, known in the art as a frame buffer for storing image data arrays. The computer system 40 is linked to a disk storage 50 and a tape drive 52 for storage of image data and programs. The computer system 40 communicates with the system controller 60 over a high-speed serial data communications link 54.

The system controller 60 also comprises a number of modules, which communicate with each other through a backplane 62. The modules of system controller 60 comprise a CP module 64, a pulse generator module 66, a transceiver module 68, a memory module 70 and an array processor module 72. The pulse generator module 66 communicates with the operator console 20 over a serial data communications link 74.

The gradient amplifier system 80 comprises Gx, Gy and Gz gradient amplifiers 82 to 86 respectively. The gradient amplifiers 82 to 86 receive input gradient pulse data from the system controller 60 and generate output gradient pulses that are conveyed to the MRI machine 120.

The RF coil control circuit 100 includes an output RF amplifier 102, an input RF preamplifier 104 and a transmit/receive (T/R) switch 106. The output RF amplifier 102 and input RF preamplifier 104 communicate with the transceiver module 68 of the system controller 60. The T/R switch 106 is coupled to the MRI machine 120 and to the RF amplifier 102 and RF preamplifier 104.

The MRI machine 120 includes a cryostat 121 having a bore 122 to receive a patient P supported on table 123. A magnet assembly 124 and RF coils 126 are disposed within the MRI machine 120. The magnet assembly 124 includes a polarizing electromagnet 128 to generate a uniform static polarizing magnetic field $B_0$ and gradient coils 130 that are responsive to the output gradient signals generated by the gradient amplifiers 82 to 86. Each gradient coil 130 is associated with a respective one of the gradient amplifiers. The RF coils 126 are coupled to the T/R switch 106.

In addition to the above components, the MRI system 10 comprises a physiological acquisition controller 140, a scan room interface circuit 142 and a patient positioning system 144. The physiological acquisition controller 140 is coupled to the pulse generator module 66 and to the MRI machine 120. The scan room interface circuit 142 is coupled to the pulse generator module 66, the patient positioning system 144 and the MRI machine 120. The patient positioning system 144 is also coupled to the MRI machine 120. The physiological acquisition controller 140 receives signals from a number of different sensors connected to the patient P, such as ECG signals from electrodes attached to the patient, and conveys the signals to the pulse generator module 66. The scan room interface circuit 142 receives input from various sensors associated with the condition of the patient and the magnet assembly 124 and conveys the signals to the pulse generator module 66. The patient positioning system 144 receives commands from the scan room interface circuit 142 and in response moves the patient P within the MRI machine 120 to the desired location for the scan.

The general operation of the MRI system 10 will firstly be described for ease of understanding. During imaging, the patient P within the MRI machine 120 is subjected to a uniform static polarizing magnetic field $B_0$ produced by the polarizing electromagnet 128. RF pulses are then generated by the RF coils 126 in a particular sequence and are used to scan target tissue of the patient. MRI signals radiated by excited nuclei in the target tissue in the intervals between consecutive RF pulses are sensed by the RF coils 126. During this MRI signal sensing, the polarizing magnetic field is altered by the gradient coils 130 in response to received output gradient data thereby to position encode acquired MRI signals.

The sequence of RF pulses used to scan the patient P is generated by the RF coils 126 in response to pulse sequence data received from the pulse generator module 66 of the system controller 60 via the transceiver module 68 and RF coil control circuit 100. The pulse sequence data determines the timing, strength and shape of the RF pulses in the pulse sequence as well as the MRI signal acquisition window. The RF sequence data is generated by the pulse generator module 66 in response to scan commands received from the operator console 20 via the data communications link 74.

When an RF pulse is to be applied to the target tissue, the RF coil control circuit 100 is conditioned to a transmit mode by the pulse generator module 66. In the transmit mode, the T/R switch 106 couples the output RF amplifier 102 to the RF coils 126. RF pulse data generated by the pulse generator module 66 is converted into an RF pulse via the transceiver module 68 and RF amplifier 102 and applied to the RF coils 126.

The pulse generator module 66 also generates gradient data in response to the scan commands received from the operator console 20 via the data communications line 74 and conveys the gradient data to the gradient amplifier system 80. The gradient data determines the timing and shape of the output gradient pulses generated by the gradient amplifiers 82 to 86 that are applied to the gradient coils 130 during scanning.

During MRI signal sensing in the MRI signal acquisition window, the pulse generator module 66 conditions the RF coil control circuit 100 to a receive mode. In the receive mode, the T/R switch 106 couples the input RF preamplifier 104 to the RF coils 126.

The MRI signals radiated by excited nuclei in the target tissue are sensed by the RF coils 56 and conveyed to the transceiver module 68 via the T/R switch 106 and input RF preamplifier 104. The amplified MRI signals are in turn demodulated, filtered and digitized by the transceiver module 68 and then transferred to the memory module 70.

After a scan of the target tissue is completed, an array of raw k-space data is stored in the memory module 70. The array processor 72 Fourier transforms the raw k-space data into an array of image data that is conveyed through the serial data communication link 54 to the computer system 20 where it is stored in the disk memory 50. In response to commands received from the operator console 20, the image data may be archived on the tape drive 52, or it may be further processed by the image processor 44 and conveyed to the operator console 20 for presentation on the display 26.

Figure 2:
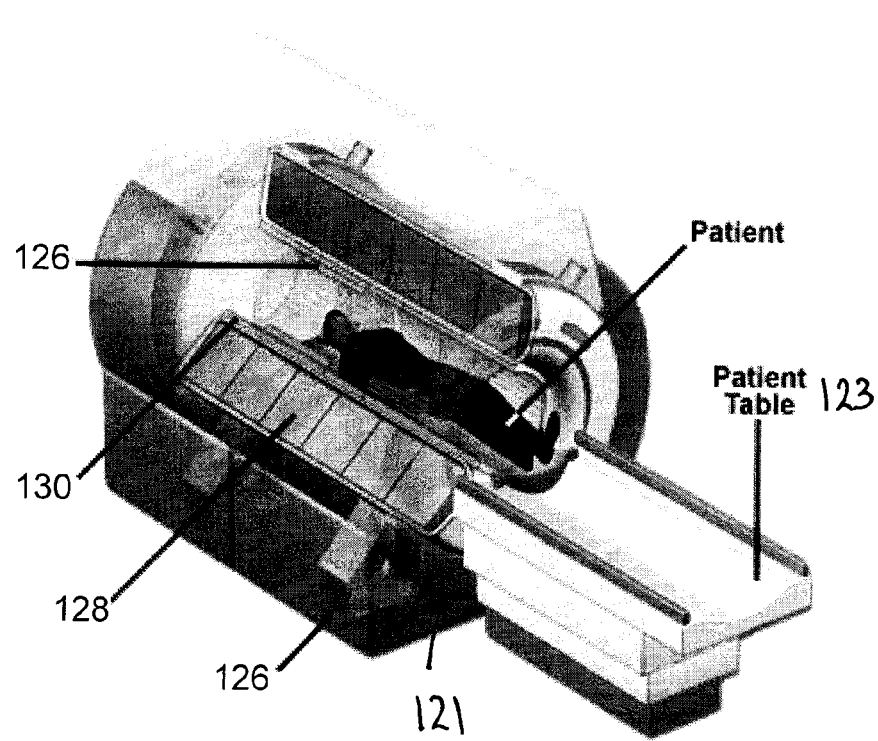
FIG. 2 is a cutaway view of an MRI machine forming part of the MRI system of FIG. 1.

FIG. 2 is a cutaway view of the MRI machine 120 and illustrates the spatial positioning of the polarizing electromagnet 128, RF coils 126, and gradient coils 130 within the MRI machine 120.

The system and method described herein provide increased specificity in magnetic resonance (MR) molecular imaging by utilizing an auxiliary magnetic field to modify the strength of the main polarizing magnetic field as a function of time in an otherwise standard MRI machine. The response in relaxivity of activated contrast agents to the auxiliary magnetic field allows for improved imaging of activated contrast agents within an MR image.

Contrast-enhanced MRI can generally be categorized as either positive or negative contrast. In positive contrast, image intensity increases at sites of MR contrast agent accumulation as a result of the dominating effect of a decreased longitudinal relaxation time $T_1$. In negative contrast, image intensity decreases at sites of MR contrast agent accumulation as a result of the dominating effect of a decreased transverse relaxation time $T_2$ (3). For illustrative purposes, the system and method will be described using activatable $T_1$ contrast agents.

The strength of a $T_1$ contrast agent can be described by its longitudinal relaxivity, $r_1$ ($s^{-1}$ $mM^{-1}$); the larger the relaxivity $r_1$, the greater its efficiency at increasing the longitudinal relaxation rate ($R_1 = 1/T_1$) of surrounding tissues and the greater its ability to enhance contrast in $T_1$ weighted MR images. The longitudinal relaxation rate ($R_1$) of a tissue which has taken up a $T_1$ contrast agent of concentration [CA] and relaxivity $r_1$ can be written as $R_1 = R_{1 Unenhanced} + r_1 \cdot [CA]$, where $R_{1 Unenhanced}$ signifies the relaxation rate of unenhanced tissue at a particular polarizing magnetic field strength $B_0$.

The rate of molecular tumbling of a contrast agent in tissue is a factor in determining the relaxivity, $r_1$ (4). Rapidly tumbling molecules exhibit lower relaxivities (typically <10 $s^{-1}$ $mM^{-1}$) that decline gradually with increasing magnetic field strengths above 0.5 T. Activatable contrast agents are designed to bind more specifically and strongly to certain proteins or classes of proteins or other macromolecular or cellular entities. Upon binding, the resulting decreased tumbling rate has been shown to produce a dramatic increase in relaxivity $r_1$ at low magnetic field strengths (e.g. less than about 0.5 T), with relatively little enhanced relaxivity at higher field strengths (e.g. above 3 T).

Figure 3:
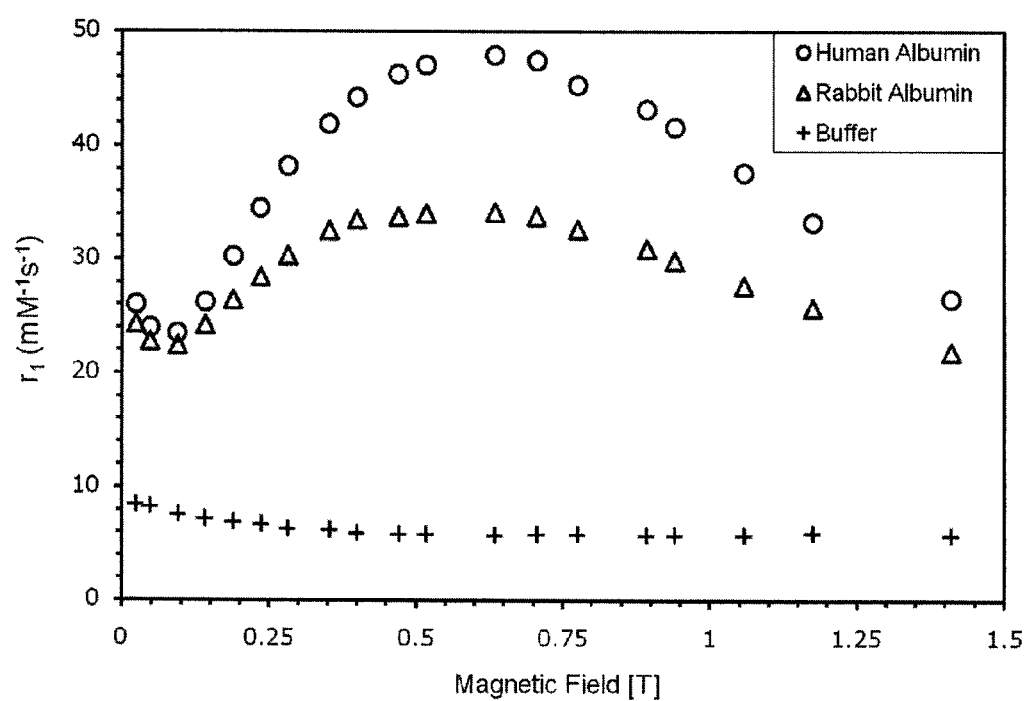
FIG. 3 is a graph of relaxivity as a function of field strength for the activatable contrast agent Vasovist alone (+) or in the presence of human (o) or rabbit (Δ) serum albumin.

Vasovist or MS-325 (Bayer HealthCare Pharmaceuticals, Gadofosveset trisodium) is one particular example of a gadolinium chelate of similar size to conventional Gd-DTPA. By virtue of the addition of a lipophilic diphenylcyclohexyl group, this molecule shows strong non-covalent binding to human serum albumin (HAS) (5, 6). In the presence of human serum albumin, the bound form of this contrast agent demonstrates an increase of relaxivity by approximately an order of magnitude at 30 Mhz, and approximately four-fold at 60 MHz. The relaxivity curves of Vasovist in the presence and absence of human serum albumin and rabbit serum albumin are shown in FIG. 3 (7). In another example, the contrast agent bis-5-HT-DTPA(Gd) has been developed as a "sensor" of the enzyme myeloperoxidase (8). In the presence of active myeloperoxidase, this contrast agent converts from a monomeric form with minimal protein binding characteristics and relaxivity similar to that of Gd-DTPA, to an oligomeric form with stronger protein binding affinity, leading to enhanced relaxivity. Another gadolinium-based contrast agent EP-2104R (Epix Pharmaceuticals), is currently in clinical trials (9). This contrast agent will selectively bind to fibrin, a significant component of blood clots (thrombi). Upon binding, contrast agent EP-2104R demonstrates a 2.3-times increase in relaxivity at a magnetic field strength equal to 1.5 T.

These three examples of gadolinium-based contrast agents represent the promise of activatable MRI contrast agents, but also illustrate a limitation of this class of agents. That is, the activation-induced relaxivity enhancement may be relatively modest, especially at clinical magnetic field strengths of 1.5 T or 3 T. As a result, it may be difficult to separate intensity enhancement due to the presence of the activated contrast agent from intensity enhancement due to the presence of larger amounts of the non-activated contrast agent.

To characterize the efficacy of an activatable contrast agent, the relaxivity enhancement ratio, that is the ratio of the activated relaxivity to the inactivated relaxivity can be defined. For Vasovist at a magnetic field strength equal to 1.5 T, the relaxivities in the presence and absence of albumin are 19 $s^{-1}$ $mM^{-1}$ and 5.2 $s^{-1}$ $mM^{-1}$ respectively, resulting in a relaxivity enhancement ratio of 3.7. From FIG. 3 it can be seen that the Vasovist relaxivity enhancement ratio peaks in the vicinity of a magnetic filed strength equal to 0.5 T, and falls quickly for magnetic field strengths above that value.

The subject system and method can distinguish between signal intensities produced by tissues containing activated contrast agent from other sources of signal intensity, using an approach termed delta relaxation enhanced MR (DREMR) (10). DREMR is an MRI method that produces image contrast related to the dependence of relaxation rate upon the strength of the applied polarizing magnetic field as a means to differentiate the activation (binding) state of a targeted contrast agent, where an activated contrast agent demonstrates magnetic field dependence while an inactivated contrast agent does not.

The DREMR approach finds its roots in field-cycling relaxometry imaging methods used by Carlson et al. (11) as a means to differentiate biological tissues. Carlson outfitted a 64 mT whole-body MRI with a pulsed electromagnet insert in order to modulate the strength of the main polarizing magnetic field during an imaging experiment. Carlson was able to show that at low magnetic field strengths the $R_1$ profiles of biological tissues contained features such as cross relaxation peaks and quadruple dips (12).

While Carlson used low-field $R_1$ field variations to identify biological tissues, the system and method described herein utilize the relative lack of $R_1$ field dependence of tissues (13, 14) at higher magnetic field strengths (for example, magnetic field strengths greater than about 0.5 T) to suppress signals from both unenhanced tissues and tissues enhanced by an inactivated contrast agent probe.

Defining $R_1'$ and $r_1'$ as the partial derivatives of $R_1$ and $r_1$ with respect to the polarizing magnetic field $B_0$ results in $R_1'=R_{1\,Unenhanced}'+r_1'*[CA]$. Applying the approximation that $R_1'_{Unenhanced} \approx 0$ for magnetic fields above 1.0 T, results in the expression $R_1' \approx r_1'*[CA]$. This simple relation shows that the rate of change of the longitudinal relaxation rate ($R_1'$) depends almost exclusively on the rate of change of contrast agent relaxivity ($r_1'$) with magnetic field. While activated contrast agents demonstrate high values of $r_1'$, inactivated contrast agents have $r_1'$ values close to zero (FIG. 3). For Vasovist, the relaxivity slope enhancement ratio (ratio of activated $r_1'$ to inactivated $r_1'$) is 90 at a magnetic field strength equal to 1.5 T. This represents a 25-fold increase over the absolute relaxivity enhancement ratio of 3.7 mentioned above. The high specificity of DREMR enhancement is not specific to Vasovist but applies to any $T_1$ contrast agent that undergoes binding to large molecules (15).

Transforming $R_1'$ into image contrast requires the ability to dynamically vary the strength of the main polarizing magnetic field in an MRI system. Access to such platforms is limited to a handful of sites worldwide (16-18). A more accessible and convenient approach described herein, involves providing conventional MRI machines with the ability to generate an auxiliary magnetic field ($\Delta B$) to enable variable polarizing magnetic field operation. One such approach involves providing the MRI machine with an electromagnetic coil insert ($\Delta B$ insert) to enable variable polarizing magnetic field operation. Another approach involves reprogramming a gradient coil within the MRI machine to enable variable polarizing magnetic field operation. Still another approach involves providing the MRI machine with a modified gradient coil to enable variable polarizing magnetic field operation.

The $\Delta B$ auxiliary magnetic field is applied during a relaxation portion of an MRI pulse sequence. For convenience, the $\Delta B$ magnetic field is applied during the longitudinal relaxation portions ($T_1$) of the MRI pulse sequence where extremely high stability and homogeneity are not necessary. The main polarizing magnetic field is not altered by the $\Delta B$ auxiliary magnetic field during actual signal sensing or any RF pulse application. This means that the normal RF transmit/receive chain can be used without modification. In the following paragraphs, the theory and an experimental demonstration of DREMR are presented, using a small-bore actively-shielded field-cycling electromagnet within an otherwise conventional 1.5 T clinical MRI machine.

Figure 4:
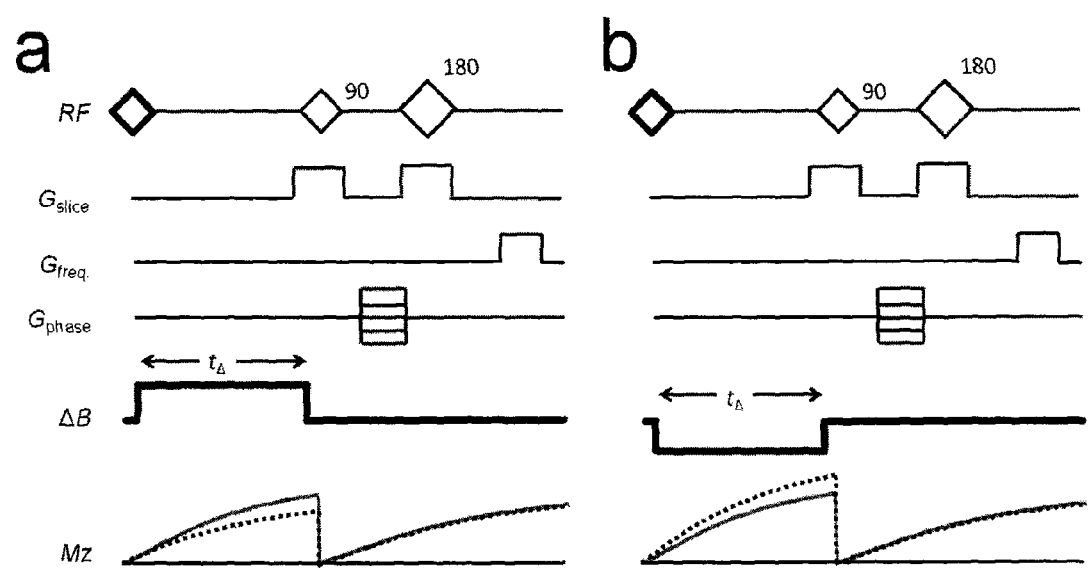
FIG. 4 is a schematic of (a) the $T_{1+}$ sequence and (b) the $T_{1-}$ sequence of spin-echo pulse sequences where an auxiliary-magnet-induced ΔB magnetic field pulse of duration tΔ has been used to modify the strength of the static $B_0$ field during a $T_1$ relaxation portion of the sequences.

Various methods can be employed to generate DREMR contrast. The simplest method involves the weighted subtraction of two $T_1$ weighted images, each image acquired with a slightly different MRI pulse sequence. These MRI pulse sequences, referred to as the $T_{1+}$ and $T_{1-}$ sequences, both resemble $T_1$ weighted sequences; however, in the $T_{1+}$ sequence a magnetic field increasing $\Delta B$ auxiliary magnetic field pulse is applied during longitudinal relaxation, while in the $T_{1-}$ sequence a magnetic field decreasing $\Delta B$ auxiliary magnetic field pulse is used. In FIG. 4, the $T_{1+}$ and $T_{1-}$ sequences are shown. Each pulse sequence contains a relaxation portion where the static polarizing magnetic field strength ($B_0$) is either increased or decreased by an amount $\Delta B$, as well as a self-contained signal sensing or acquisition portion, which may be a conventional imaging sequence such as, spin-echo, fast spin-echo, etc. In this example a spin-echo signal acquisition portion is shown.

On the final line of FIG. 4 the longitudinal magnetization of two theoretical tissues is shown. The $R_1$ magnetization rate of the tissue represented by the solid curve is nearly independent of magnetic field strength and therefore relaxes identically for both the $T_{1-}$ and $T_{1+}$ sequences. However the $R_1$ magnetization rate of the tissue represented by the dashed curve is highly dependent upon the strength of the magnetic field; increasing at lower magnetic field strengths and decreasing at higher magnetic field strengths. Subtraction of the images produced by the $T_{1-}$ and $T_{1+}$ sequences would result in an image where the only intensity would be due to the magnetic field dependent tissue (dashed curve). The other tissue would be completely suppressed (solid curve).

The following analytic treatment is provided to help describe this method. To simplify the analytic treatment it is assumed that each relaxation portion begins with a saturation RF pulse to eliminate any preexisting longitudinal magnetization; however, other initialization states could be used in a similar analysis. The effect of finite ramping times for the $\Delta B$ auxiliary magnetic field pulse will be ignored. Starting at Curie's Law, the steady state longitudinal magnetization ($M_0$) is proportional to the amplitude of the applied magnetic field. Following the completion of a ΔB auxiliary magnetic field pulse of duration $t_\Delta$ the longitudinal voxel magnetization (Mz) is equal to $M_0 \cdot \exp(1-t_\Delta \cdot R_1)$. Besides effecting $R_1$, modification of the polarizing magnetic field $B_0$ results in the longitudinal voxel magnetization Mz being reduced by a factor of $(B_0-\Delta B)/B_0$ by the negative ΔB auxiliary magnetic field pulse, and increased by a factor of $(B_0+\Delta B)/B_0$ by the positive ΔB auxiliary magnetic field pulse. In the following, longitudinal magnetization formulae the + and − subscripts on $M_z$, will indicate whether the longitudinal voxel magnetization $M_z$ was formed during a positive or negative ΔB auxiliary magnetic field pulse. $R_{1-}$ will indicate the longitudinal relaxation rate of the sample at the reduced polarizing magnetic field strength of $B_0-\Delta B$, while $R_{1+}$ indicates the $R_1$ at an increased polarizing magnetic field strength. Note that $R_{1-}$ may be greater than $R_{1+}$. The longitudinal voxel magnetization following negative and positive ΔB auxiliary magnetic fields are expressed by Equations [1] and [2] below:

$$M_{z-} = M_0 \cdot \frac{B_0 - \Delta B}{B_0}[1 - \exp(-t_\Delta \cdot R_{1-})] \quad [1]$$

$$M_{z+} = M_0 \cdot \frac{B_0 + \Delta B}{B_0}[1 - \exp(-t_\Delta \cdot R_{1+})] \quad [2]$$

Image voxel intensity is determined by the combined actions of the signal acquisition module, MRI machine signal detection hardware, and console software. For simplicity it will be assumed that the final image intensity is a product of the actual voxel magnetization ($M_z$), and a single positionally dependent term, k, that incorporates proton density, RF coil homogeneity, transverse relaxation time, and any other scaling factors. The resulting image intensity (absolute value) in each pixel I(x, y) is then related to voxel magnetization and expressed as $I(x, y)=k(x, y, r) \cdot M_z(r)$. Forming the DREMR image requires taking the weighted difference of the $I_-$ and $I_+$ images. Due to the different equilibrium magnetization introduced by the perturbation magnetic field, the image magnitudes $I_-$ and $I_+$ must be normalized prior to subtraction:

$$I_{Sub.} = I_- \frac{B_0}{B_0 - \Delta B} - I_+ \frac{B_0}{B_0 + \Delta B} \quad [3]$$

If the assumption is made that $R_1'$ is constant in the vicinity of $B_0$ then it is possible to approximate the resulting image intensity by the following expression, wherein $\Delta R_1$ is the absolute change in $R_1$ from $B_0$ to $B_0 \pm \Delta B$:

$$I_{Sub.} \approx 2k \cdot M_0 \cdot \sin h(t_\Delta \cdot \Delta R_1) \cdot \exp(-t_\Delta \cdot R_1) \quad [4]$$

There are two non-linear terms in Equation 4, namely the hyperbolic sine and exponential decay functions. The hyperbolic sine term, though non-linear, is responsible for the distinctive contrast produced by this method. It indicates that difference in intensity between voxels in the final DREMR image will be related to the $R_1'$ values of those voxels.

The exponential decay function results in image shading when the longitudinal relaxation time $t_\Delta$ is set too long and the voxel magnetizations of the $I_-$ and $I_+$ images begin to saturate. This is comparable to using a $T_R$ much longer than $T_1$ when taking a $T_1$ weighted image. If $t_\Delta$ is chosen so that the maximum product of $t_\Delta \cdot R_1$ is less than 0.2, then maximum shading is limited to at most 20 percent. In the same way, if $t_\Delta$ is chosen so that the maximum product of $t_\Delta \cdot \Delta R_1$ is less than 0.5 then nonlinearity effects are limited below 5%. Equation 5a shows that with the appropriate choice of $t_\Delta$ image intensity becomes linear with $\Delta R_1$. Equation 5b expresses the result more explicitly with $\Delta R_1$ replaced by the product of $R_1'$ and ΔB; that is, the slope of $R_1$ multiplied by the strength of the magnetic field shift:

$$I_{Sub.} \approx 2k \cdot M_0 \cdot t_\Delta \cdot \Delta R_1 \quad [5a]$$

$$I_{Sub.} \approx 2k \cdot M_0 \cdot t_\Delta \cdot \Delta B \cdot R_1' \quad [5b]$$

This is the simplest implementation of DREMR. With this implementation, it is possible to produce image intensities that depend on the change in $R_1$ rather than in $R_1$ itself. Activatable contrast agents of the types described herein all produce major changes in $R_1'$ upon activation, even if the enhancement in $R_1$ is much smaller. This mathematical basis for one implementation of DREMR illustrates its potential application to the specific imaging of activatable MRI contrast agent probes.

DREMR results in a reduction of signal to noise ratio (SNR). Because of the restrictions placed previously, that is $t_\Delta \cdot R_1 < 0.2$, the SNR of the constituent images, $I_-$ and $I_+$, after normalization can be approximated as $k \cdot M_0 \cdot t_\Delta \cdot R_1/\sigma$ where σ is uncertainty in the images after normalization. Dividing Equation 5b by σ gives the SNR of the DREMR image. This result can be written in terms of the SNR of the source images as:

$$SNR_{Sub.} \approx \sqrt{2} \cdot \Delta B \cdot R_1'/R_1 \cdot SNR \quad [6]$$

Equation 6 again involves an approximation; it is assumed the magnetic field shifts about $B_0$ are small enough such that the uncertainties of the L and images are identical. When the magnetic field shifts are larger, the SNR equation must take into account the different uncertainties in each image.

For an $R_1' \cdot \Delta B$ ($\Delta R_1$) of 1 s$^{-1}$ and an $R_1$ of 10 s$^{-1}$, the SNR of the DREMR image drops to 14% of the SNR of the source image. Beyond simply gauging the loss in SNR, Equation 6 illustrates that the maximum SNR would be produced by contrast agents that demonstrate a sharp change in $r_1$ (large $r_1'$) for a small value of $r_1$. Evaluation of the $r_1'/r_1$ of a molecular probe may provide a basis for evaluating which molecular probes would benefit from DREMR contrast.

This derivation has outlined the most basic method to produce DREMR contrast. Other more complicated methods could certainly be applied. A double subtraction method for example could utilize several inversion pulses as well as several ΔB auxiliary magnetic field pulses to achieve DREMR contrast without subtraction.

The DREMR approach is now illustrated with reference to the following examples that provide experimental and computer simulated results.

Example 1

To demonstrate the feasibility of the DREMR approach, the contrast agent Vasovist (MS-325) was imaged in the presence and absence of rabbit serum albumin (RSA). As shown in FIG. 3, Vasovist preferentially binds to albumin, producing moderate enhancement in the inactivated state and higher enhancement in the activated state. The particular choice of agent/protein pair was based by the availability of the contrast agent and its well-documented relaxivity mechanisms, rather than any specific clinical or research interest in albumin.

An MRI phantom (see FIG. 5a) was constructed that held two columns of six rows of glass tubes; each tube 3 cm in length with a 0.4 mL capacity. The sample tubes in the left column were filled with 0.01 M phosphate buffered saline (PBS) (NaCl 0.138M, KCl 0.0027M, pH 7.4 at 25° C.). The right column of sample tubes held a solute of rabbit serum albumin (Sigma-Aldrich, batch 104K7560, agarose gel electrophoresis) in PBS. The albumin, purchased as a lyophilized powder, was dissolved in PBS, at a 4.5% weight to volume ratio resulting in ~0.67 mM concentration. Vasovist (0.25 mmol/mL) was added in equal concentration to both columns to achieve sample concentrations of 0, 10, 20, 40, 80 and 160 µM as a function of descending rows.

Imaging was performed on a Sigma LX 1.5 T clinical MRI machine (General Electric Healthcare), equipped with an actively shielded electromagnetic ΔB insert (19). The ΔB insert, designed to generate±ΔB auxiliary magnetic field pulses, had an efficiency of 0.7 mT/A, weighed approximately 150 kg and was designed to facilitate the imaging of animals as large as rabbits. The ΔB insert was driven by a pair of Techron 8607 gradient amplifiers arranged in a master/slave series configuration enabling a maximum bipolar output of 100 A. Input waveforms to the gradient amplifiers were generated by National Instruments data acquisition hardware and controlled via software written in LabView (National Instruments, version 8.2). Waveform synchronization between the data acquisition device and the MRI console was achieved by means of the 'scope trigger' output of the console electronics.

The following spin-echo pulse sequence parameters were used for all images that were combined to produce the final DREMR image: 150 ms pulse repetition time, 10 ms echo time, 31 kHz bandwidth, 8 cm field of view and 10 mm slice thickness. The scan time was 24 s for each image. For each row of k-space, 70 mT ΔB auxiliary magnetic field pulses were applied for 100-ms intervals. The ΔB auxiliary magnetic field pulses were timed to end 10 ms prior to image acquisition to give both the polarizing magnetic field and amplifiers time to stabilize.

For $T_{1+}$ images the polarizing magnetic field was increased by 70 mT during the relaxation portion of the MRI pulse sequence. Likewise for $T_{1-}$ images the polarizing magnetic field was decreased by the same amount. Ten pairs of $T_{1+}$ and $T_{1-}$ weighted images were acquired for the samples held at 21° C. Acquisitions of $T_{1+}$ and $T_{1-}$ enhanced images were interleaved to minimize heating of the amplifiers. The positively enhanced images were then averaged into a single dataset, as were the negatively enhanced images. The resulting two datasets were normalized and the absolute difference taken to produce contrast related to the magnetic field dependence of $R_1$. Unlike in the theoretic treatment a saturation pulse was not applied prior to the ΔB auxiliary magnetic field pulse. Standard $T_1$ weighted spin-echo images using the same MRI pulse sequence parameters were acquired for comparison.

Figure 5:
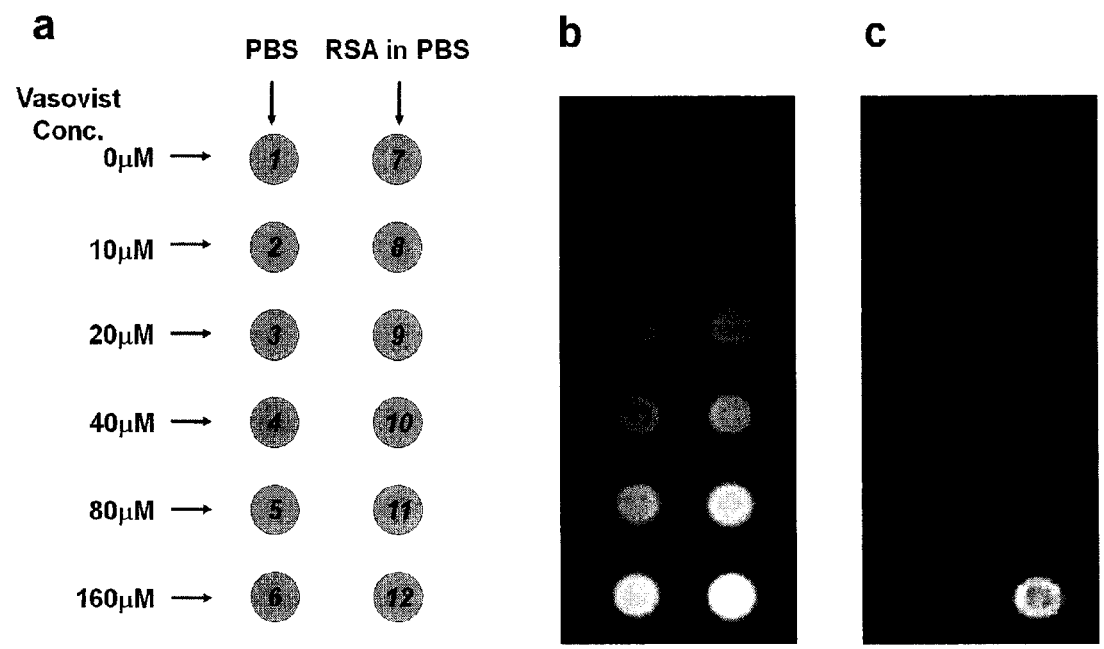
FIG. 5 shows (a) an experimental sample and its MRI resulting in (b) a conventional $T_1$ weighted image and (c) a $T_1$ weighted image using the system and method described herein.

FIG. 5b shows the standard $T_1$ weighted spin-echo image of the samples. As expected, the intensity of both columns increased from top to bottom with concentration of Vasovist. The measured average intensity within each sample is plotted in FIG. 6a. The error bar on each data point indicates the standard deviation of voxel intensity throughout the corresponding sample. Both sets of samples, albumin solution and PBS, demonstrated significant dependence on Vasovist concentration. Because the range of intensities of the albumin samples (Δ) were not clearly separated from those of the PBS samples (●) but in fact were appreciably overlapped, it is clear that without prior knowledge of Vasovist concentrations, it would not be possible to differentiate the albumin-containing sample from PBS-only samples based on $T_1$ weighted image intensity alone.

FIG. 5c illustrates the absolute difference of the ±LIB auxiliary magnetic field datasets. The figure shows the entire dynamic range without thresholding. The average intensity from each of the samples is plotted in FIG. 6b. The standard deviation of voxel intensities within each sample is again expressed as an error bar. While the image intensity of albumin samples continued to demonstrate dependence on Vasovist concentration, the PBS samples were significantly suppressed. The intensities of all PBS samples were suppressed well below the intensity of the weakest albumin-loaded sample, which had only a 10 µM Vasovist concentration. Thus a substantially increased specificity to albumin was obtained through DREMR imaging.

Figure 6:
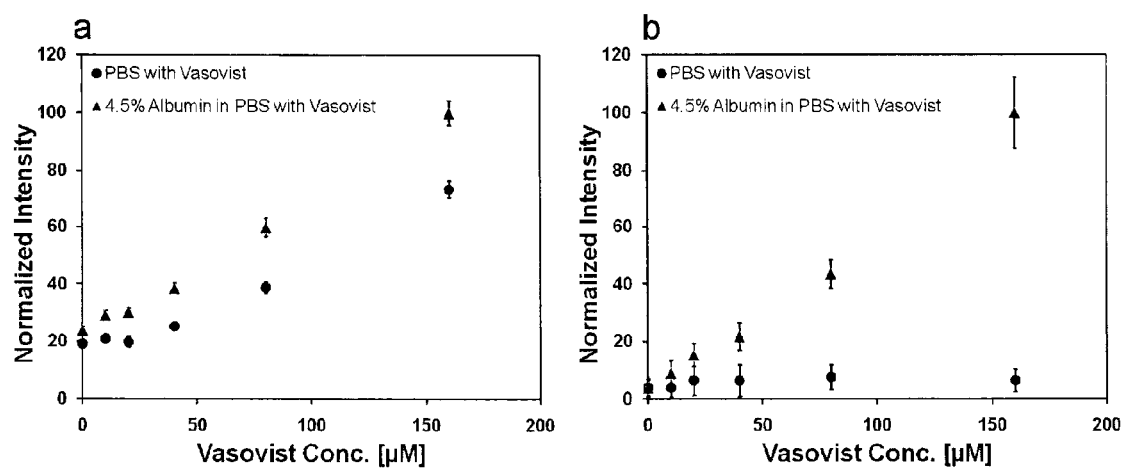
FIG. 6 graphs the sample intensities found in the images shown in FIG. 5 (b) and (c)

Intensity variations in the DREMR image were seen to increase by a factor of 2.5 times those of the $T_1$ weighted image as indicated by the larger error bars in FIG. 6b compared to FIG. 6a. This was due to the combined effects of SNR loss and introduction of subtraction artefacts. Subtraction artefacts appear as a mottling across the samples and are due to instabilities in the polarizing magnetic field $B_0$ during image acquisition; instabilities most likely introduced by rapid switching of the ΔB insert. Subtraction artefacts were localized to positions having significant image intensity in the constituent images whereas noise increased across the entire image. Even with active shielding, minor inductive coupling between the ΔB insert and the MRI machine has the potential to produce eddy currents in the cryostat and superconductive windings of the polarizing electromagnet. These eddy currents could destabilize the main polarizing magnetic field, causing minor slice selection errors and errors in the RF tip angle. To counter this potential problem, the ΔB insert was used as an active shim during image acquisition.

Example 2

The embodiments described in this Example allow for generation of an auxiliary magnetic field, without the need for the auxiliary electromagnetic insert described in Example 1. The embodiments described in this Example involve either an unmodified MRI system or an MRI system comprising a modified gradient coil system. The modified gradient system may be used to produce both linearly varying and uniform polarizing magnetic fields across the imaging region.

Figure 7:
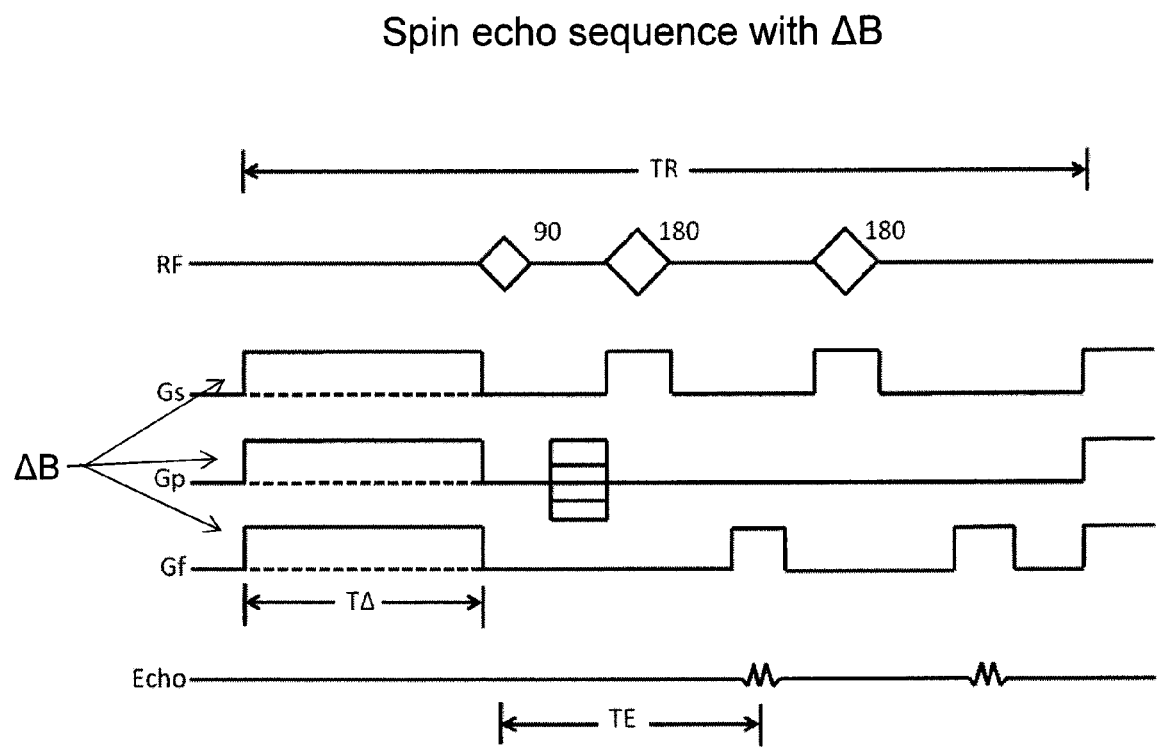
FIG. 7 is a schematic of a spin-echo pulse sequence where a gradient coil-induced ΔB magnetic field pulse of duration tΔ has been used to modify the strength of the static $B_0$ field during a $T_1$ relaxation portion of the sequence.

In FIG. 7 one embodiment is shown in which a standard spin-echo pulse sequence has been modified to include gradient-induced magnetic field pulses during the relaxation portion of the MRI pulse sequence. The choice of spin-echo pulse sequence is consistent with FIG. 4 which used a spin-echo pulse sequence to generally illustrate the timing of ΔB auxiliary magnetic field generation. FIG. 7 shows that all three gradient coils (Gs, Gp, and Gf, also known as Gz, Gx and Gy, respectively) are applied at the same time to generate ΔB auxiliary magnetic field pulses throughout time TΔ. TΔ occurs within the $T_1$ relaxation portion of the pulse sequence. (TΔ in FIG. 7 and to in FIG. 4 are used interchangeably to designate the ΔB auxiliary magnetic field pulse duration). In conventional MRI none of the gradient coils pulse during a relaxation portion of the MRI pulse sequence, as represented by the dashed lines in FIG. 7. Conventionally, gradient coils are only pulsed during an image acquisition portion of the MRI pulse sequence. For simplification, the reversal of the ΔB auxiliary magnetic field as shown in FIG. 4(b) is not shown in FIG. 7.

Figure 8:
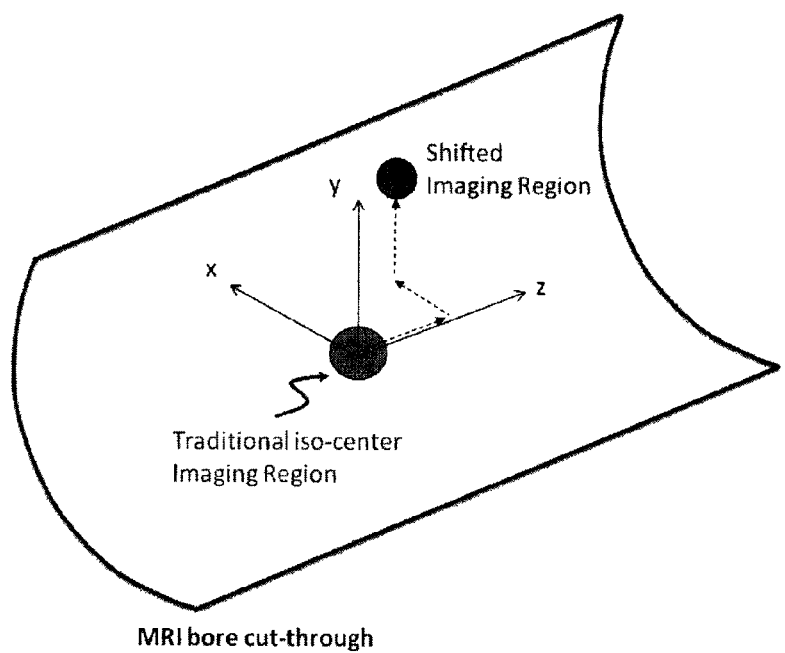
FIG. 8 shows placement of a target sample offset from the iso-center.

When an MRI machine, equipped with a traditional gradient coil set is used, the target being imaged may require placement away from iso-center (FIG. 8). The strength of the ΔB magnetic field shift produced by the unmodified gradient coil is at its maximum at the very edge of the imaging region, and therefore to optimize contrast the target being imaged may be placed at the edge of the imaging region.

Figure 9:
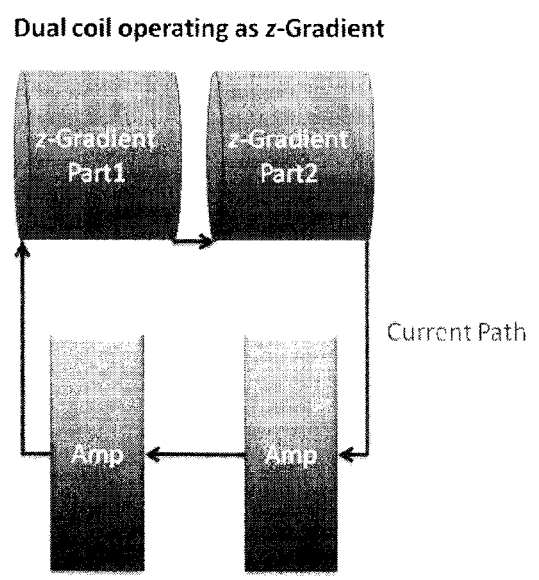
FIG. 9 shows the current path of a conventional longitudinal (i.e., z-axis) gradient coil.

In another embodiment, one or more of the gradient coils of the MRI machine are modified to generate a substantially uniform non-zero auxiliary magnetic field across the imaging region image during the relaxation portion of the MRI pulse sequence. Therefore, the positioning of the target with respect to the iso-center is not needed to optimize contrast. FIG. 9 shows a schematic of a typical unmodified longitudinal gradient coil connected to a set of amplifiers. The typical longitudinal gradient coil can be thought of as two distinct coils electrically wired in series. By electrically separating the two halves of the gradient coil and attaching each half to a separate amplifier, each half of the gradient can be independently controlled.

Figure 10:
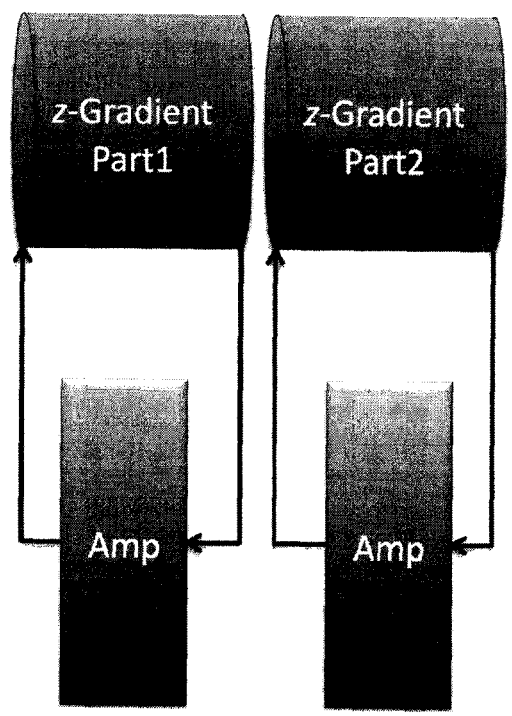
FIG. 10 shows the current path of the gradient coil shown in FIG. 9 modified in accordance with the system and method described herein, when the modified gradient coil is used to generate a varying magnetic field across an imaging region.
Figure 11:
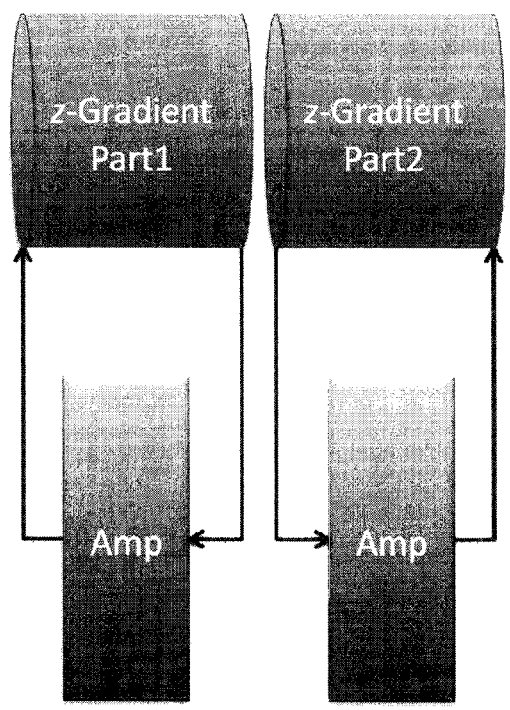
FIG. 11 shows the current path of the modified gradient coil shown in FIG. 10, when the modified gradient coil is used to produce a substantially uniform magnetic field across the imaging region.
Figure 12:
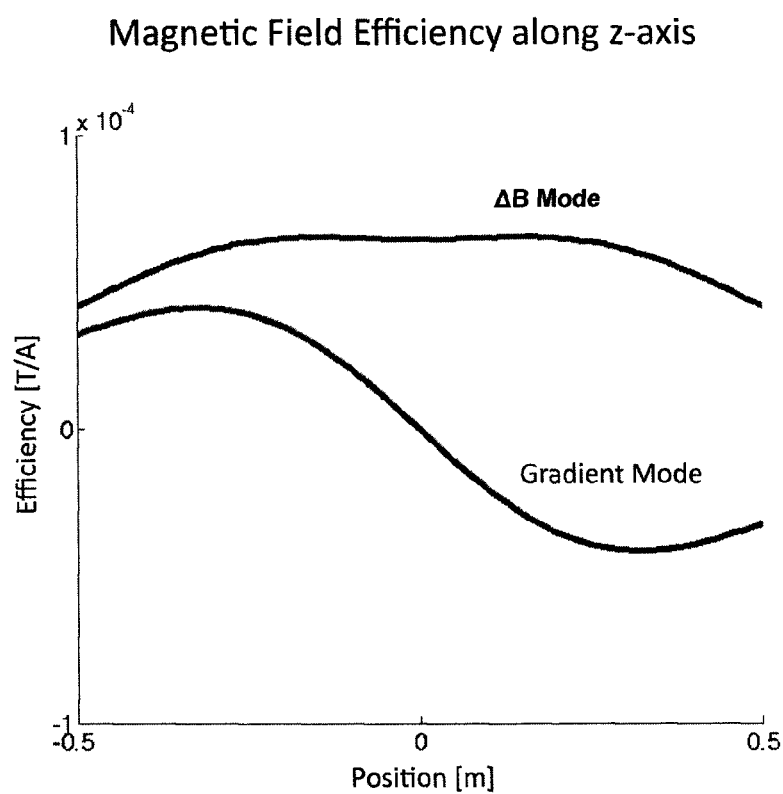
FIG. 12 is a graph showing the two magnetic fields that can be generated by the modified gradient coil shown in FIGS. 10 and 11 plotted as a function of the spatial position within the imaging region with 0 indicating the iso-center.

When both amplifiers cause current to flow with the same polarity (FIG. 10), the modified gradient coil behaves in the typical gradient coil fashion and a linearly varying magnetic field is produced for MR image formation (plotted as 'Gradient Mode' in FIG. 12). When the amplifiers cause current with opposite polarities to flow (FIG. 11) the modified gradient coil behaves as a ΔB coil, in that it generates a substantially uniform auxiliary magnetic field across the imaging region (plotted as 'ΔB mode' in FIG. 12), ideally producing a magnetic field shift that is invariant with position.

In its intended operation, a modified gradient coil will produce a constant auxiliary magnetic (ΔB) field during the relaxation portion of the MRI pulse sequence (FIG. 7) and a varying magnetic (gradient) field during the imaging portion of the MRI pulse sequence. Thus, a single gradient coil can be used to create the magnetic field shift during the relaxation portion of the MRI pulse sequence for contrast enhancement, and the varying magnetic field shift required for acquiring spatial MRI image formation.

Figure 13:
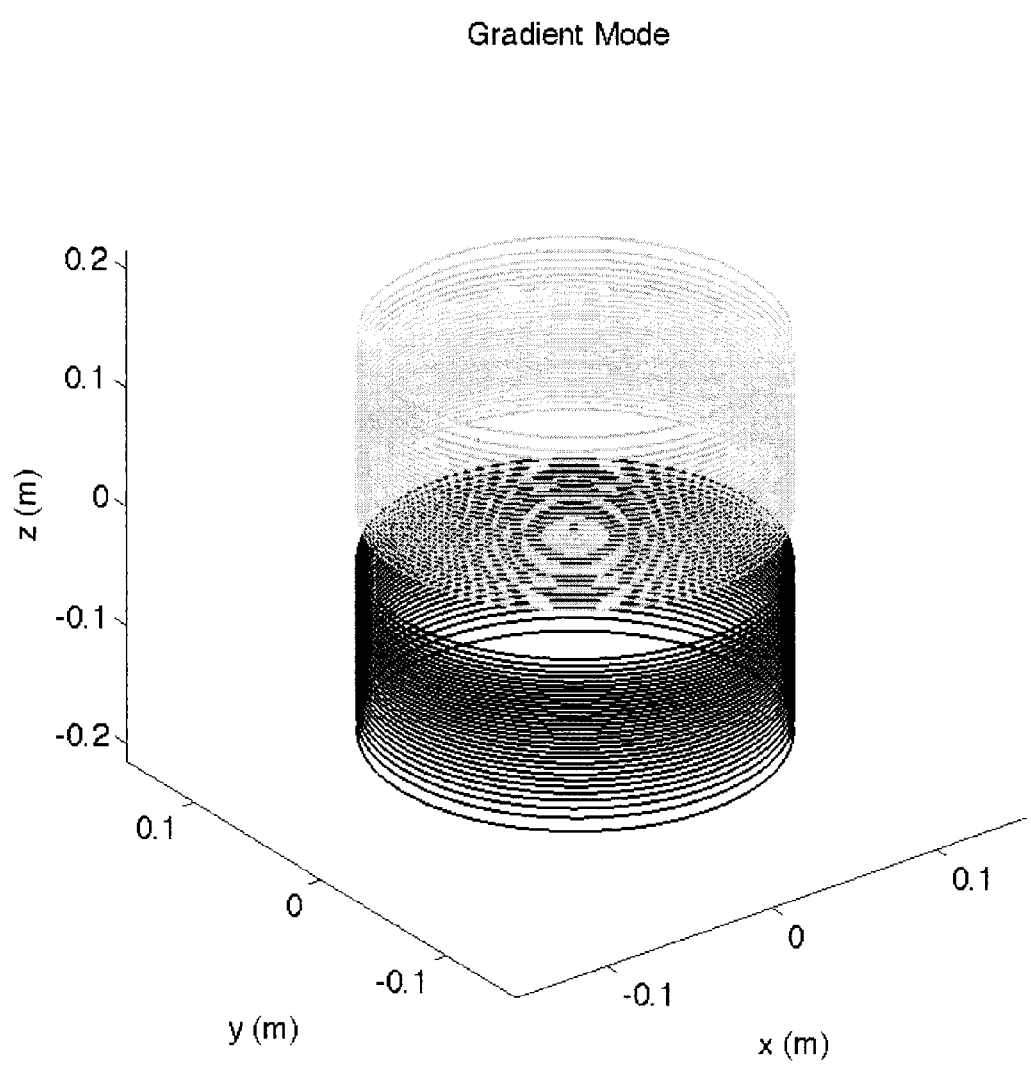
FIG. 13 shows the wire pattern and current flow of the modified gradient coil shown in FIG. 10.
Figure 14:
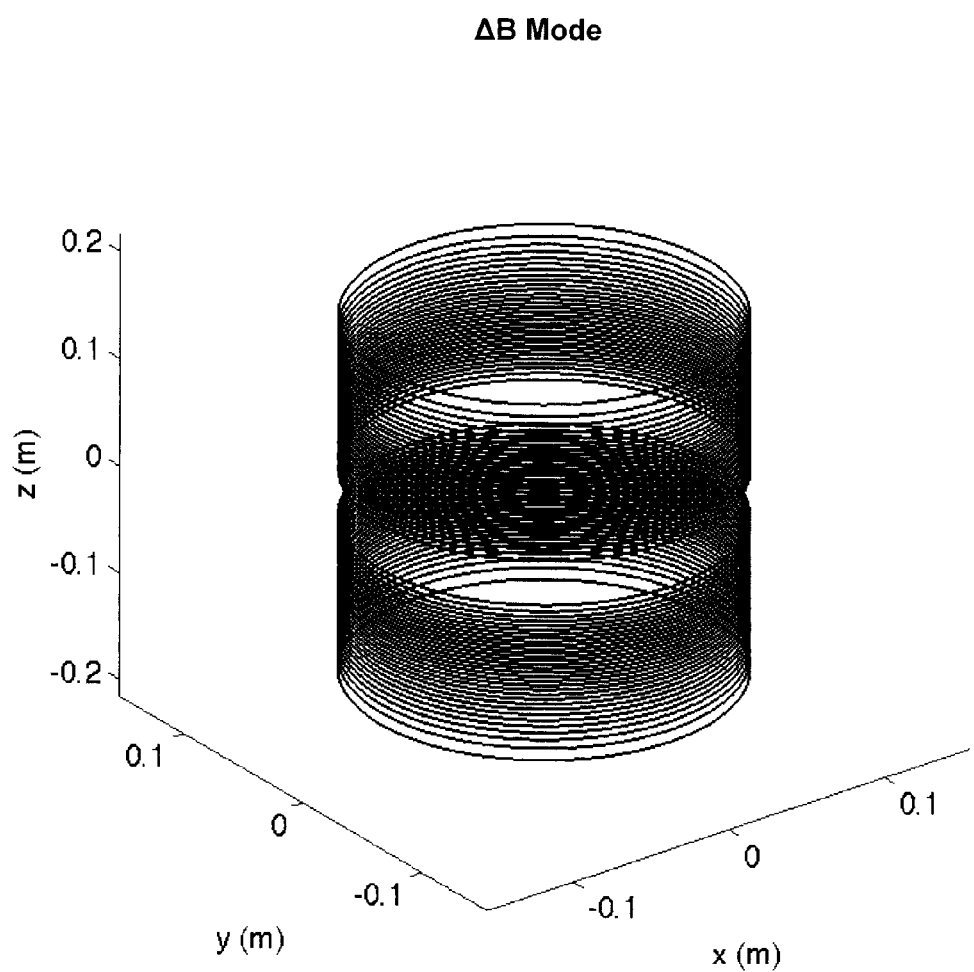
FIG. 14 shows the wire pattern and current flow of the modified gradient coil shown in FIG. 11.

FIGS. 13 and 14 show the wire pattern for one particular embodiment of a modified gradient coil. Current direction is indicated by the color coding of the wire; black indicates that current flow is parallel to the x-axis and grey indicates anti-parallel current flow. In FIG. 8, the gradient coil behaves like a traditional gradient coil. In FIG. 9 the current direction is reversed in the top half of the coil and the modified gradient coil behaves like a ΔB coil.

Figure 15:
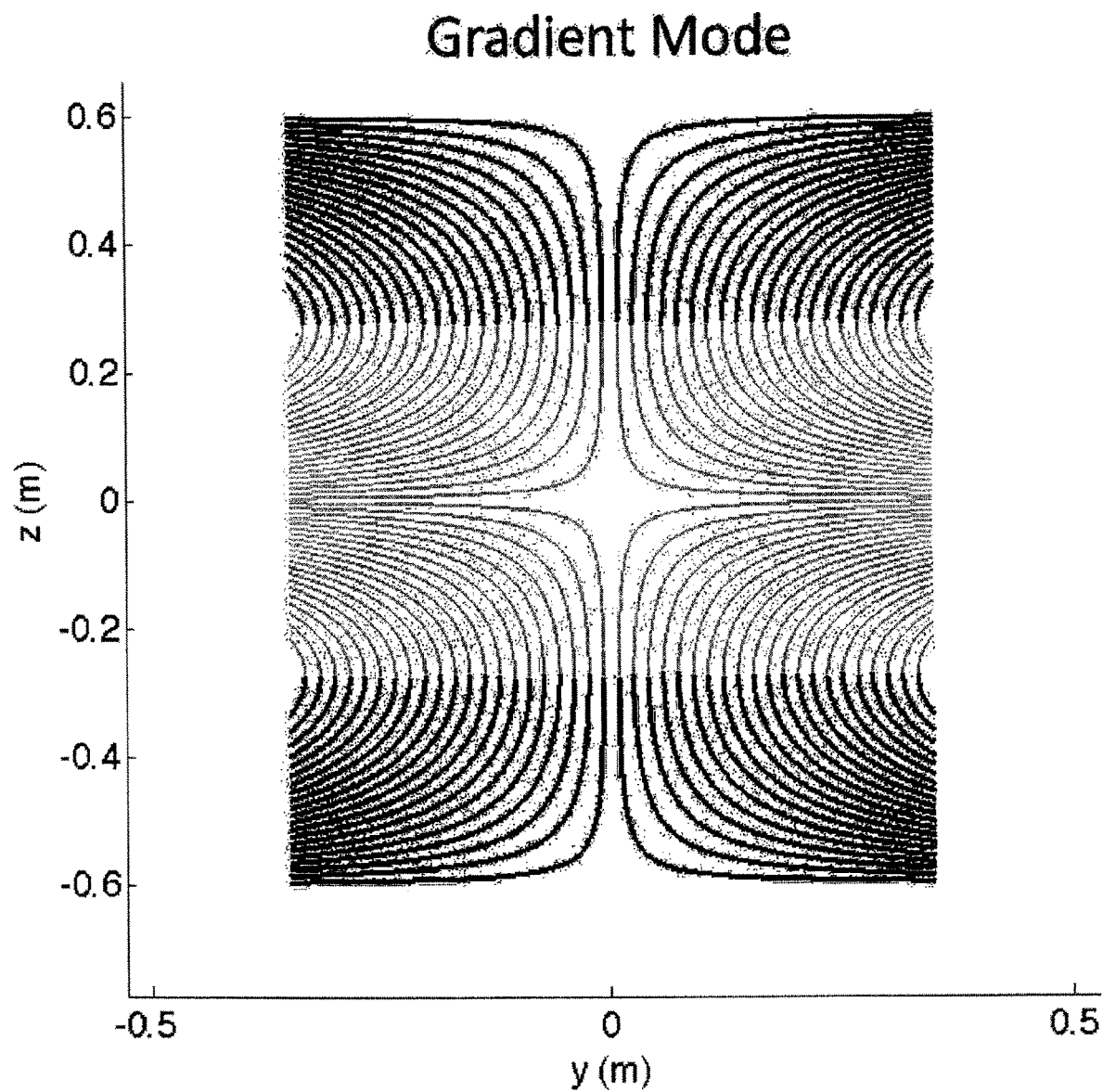
FIG. 15 shows the wire pattern and current flow of a transverse gradient coil, modified in accordance with the system and method described herein, when the modified gradient coil is used to generate a varying magnetic field across an imaging region.
Figure 16:
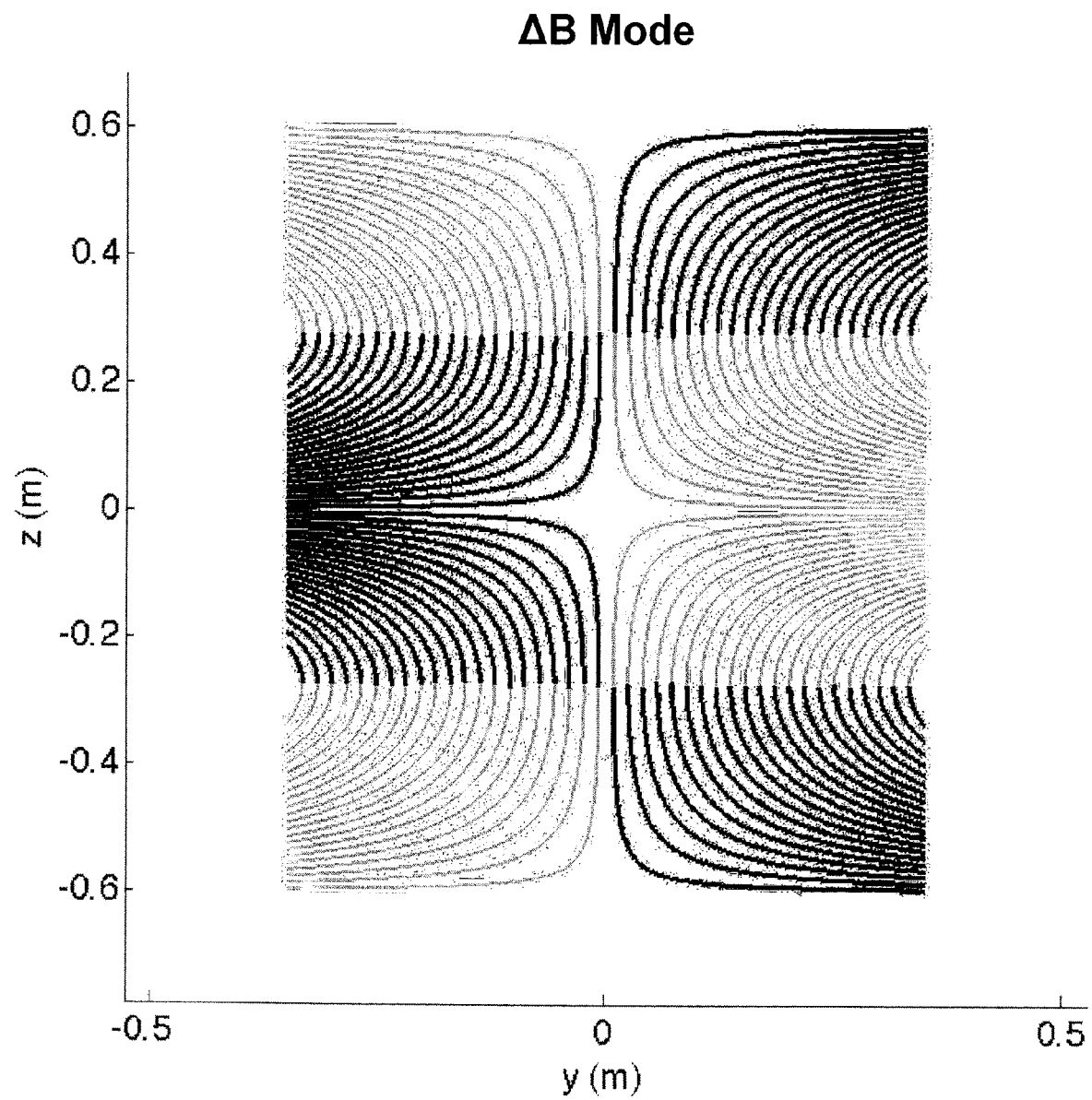
FIG. 16 shows the wire pattern and current flow of the modified gradient coil shown in FIG. 15, when the modified gradient coil is used to produce a substantially uniform magnetic field across the imaging region.

In some embodiments similar approaches may be used to modify the transverse (x and y) gradient coils to allow dual operation as either a conventional gradient coil or a ΔB coil. Current direction is indicated by the color coding of the wire; black lines indicate current flow parallel to the y-axis and grey lines indicates current flow anti-parallel to the y-axis. FIG. 15 shows the wire pattern of a particular embodiment of a transverse gradient coil when used in gradient mode. When the polarity of current is changed in half of the gradient coil only (FIG. 16), the coil acts as a ΔB coil and produces a uniform magnetic field profile.

Embodiments that provide conventional gradient coils with the target in the iso-center, conventional gradient coils with the target offset from the iso-center, and a modified longitudinal gradient coil with the target in the iso-center were analyzed using computer simulations. As a comparator, a standard $T_1$ weighted image was also produced.

Figure 17:
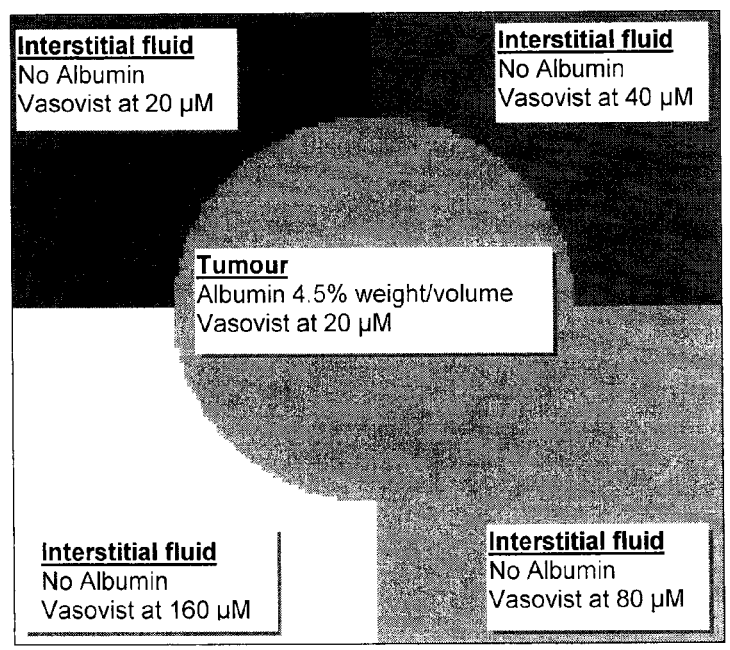
FIG. 17 shows a computer simulation of a conventional $T_1$ weighted image of a tumour over its surrounding interstitial fluid at various concentrations of the activatable contrast agent, Vasovist.

For each of the computer simulations (shown in FIGS. 17, 18, 20 and 22) the target being imaged is a tumour (represented by a circle) that is surrounded with interstitial fluid (each quadrant representing a distinct concentration of Vasovist). The tumor contains the protein albumin, which is not found in the surrounding fluid. Albumin binds to the contrast agent Vasovist. Vasovist is used to enhance the tumor, but due to leaky vasculature also enhances the interstitial fluid. Inside the tumor the concentration of Vasovist is 20 µM, while outside the tumor the concentration of Vasovist varies from 20 to 160 µM as shown in FIG. 17. The tumour and interstitial fluid Vasovist and albumin concentrations are identical for each of FIGS. 17, 18, 20 and 22.

As a comparative example, a standard $T_1$ weighted image of the tumour is shown in FIG. 17. FIG. 17 shows that standard $T_1$ weighting is insufficient to enhance the tumour over the interstitial fluid.

DREMR can be used to create image contrast that preferentially enhances locations where the protein albumin has bound the Vasovist contrast agent (e.g. inside the tumour). DREMR uses an auxiliary magnetic field shift to produce the unique contrasts. In these computer simulation examples the auxiliary magnetic field, ΔB, is achieved by the longitudinal gradient coil of the MRI system.

Figure 18:
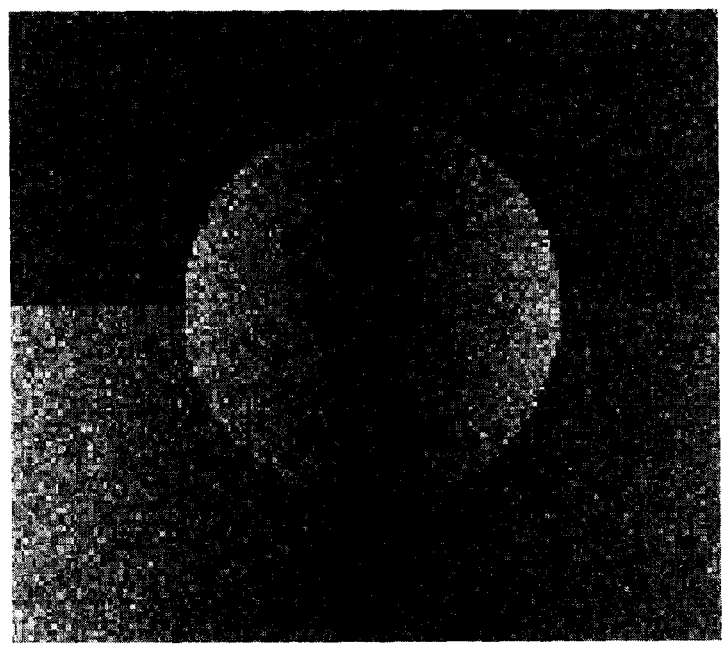
FIG. 18 shows a computer simulation of a $T_1$ weighted image of the tumour and surrounding interstitial fluid as shown in FIG. 17 obtained with the tumour positioned at the iso-center and using a conventional MRI machine with the z-gradient coil programmed to generate a ΔB magnetic field that is linearly varying across the imaging region.

FIG. 18 shows a simulated DREMR image of the tumour. The DREMR contrast has been created by applying a linearly varying magnetic field across the image. During the relaxation portion of each pulse sequence, the ΔB auxiliary magnetic field increases from −10 mT on the left to 10 mT on the right to produce a first $T_1$ weighted image. The ΔB auxiliary magnetic field is then reversed to produce a second $T_1$ weighted image. Subtraction of the first and second $T_1$ weighted images produces the DREMR image. In the conventional method used to produce the image in FIG. 17 no subtraction occurred and no ΔB auxiliary magnetic field was generated during the relaxation portion of the MRI pulse sequence.

Figure 19:
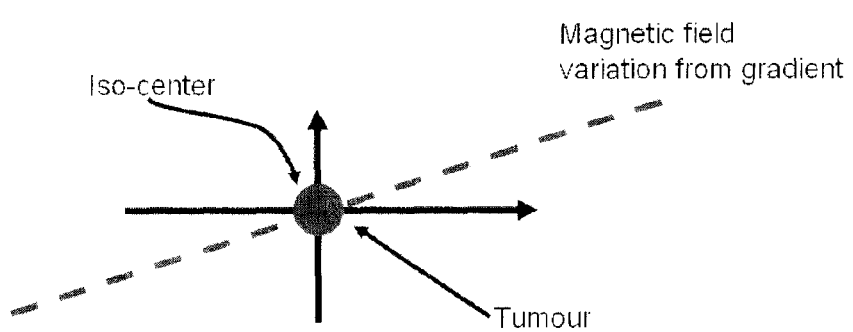
FIG. 19 shows the ΔB magnetic field and tumour position used to obtain the image shown in FIG. 18.

FIG. 19 shows the setup for FIG. 18. The tumour is located at the iso-center where the gradient magnetic field changes from positive to negative. As a result of DREMR performed in this setup, and as seen in FIG. 18, the background of the tumour has been suppressed, but the cost to image quality is quite high. More specifically, FIG. 18 shows that in the middle of the tumour (circle) there is no contrast between the tumour and the background, as the middle of the tumour coincides with the iso-center.

Figure 20:
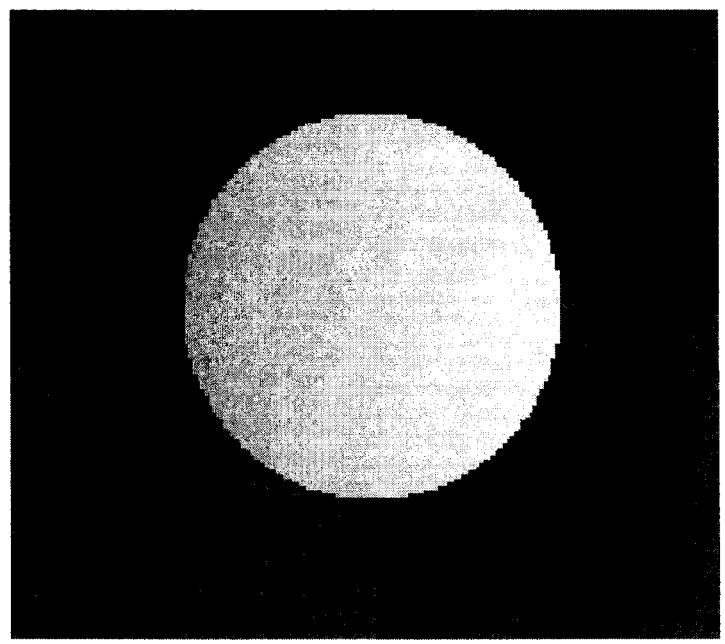
FIG. 20 shows a computer simulation of a $T_1$ weighted image of the tumour and surrounding interstitial fluid as shown in FIGS. 17 and 18 obtained with the tumour positioned offset from the iso-center and using a conventional MRI machine with the z-gradient coil programmed to generate a ΔB magnetic field that is linearly varying across the imaging region.

FIG. 20 shows a simulated DREMR image where the sample has been shifted off-axis, but is otherwise the same setup as used for FIG. 18. The ΔB auxiliary magnetic field increases from 20 mT on the left to 40 mT on the right to produce a first $T_1$ weighted image. The ΔB auxiliary magnetic field is then reversed to produce a second $T_1$ weighted image. Subtraction of the first and second $T_1$ weighted images produces the DREMR image. FIG. 20 shows a significant improvement over FIGS. 17 and 18; however some shading still exists across the tumour. Further improvements in image quality can be achieved as a function of averaging and/or offset positioning from multiple axes.

Figure 21:
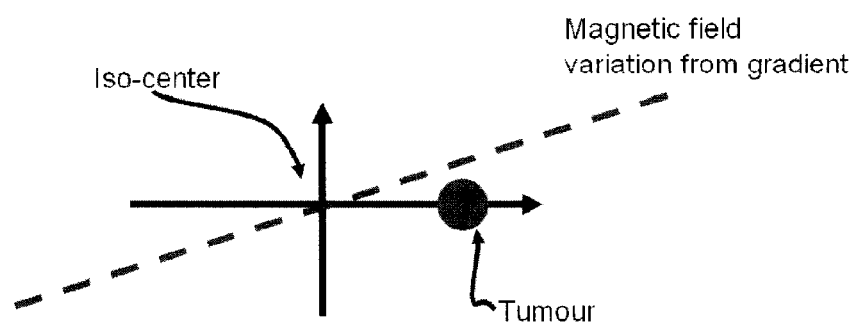
FIG. 21 shows the ΔB magnetic field and tumour position used to obtain the image shown in FIG. 20.

FIG. 21 shows the setup for FIG. 20. The tumour has been placed off-axis where the ΔB auxiliary magnetic field generated by the gradient coil during the relaxation portion of the pulse sequence is consistently positive (shown), or consistently negative when the ΔB auxiliary magnetic field is reversed (not shown).

Figure 22:
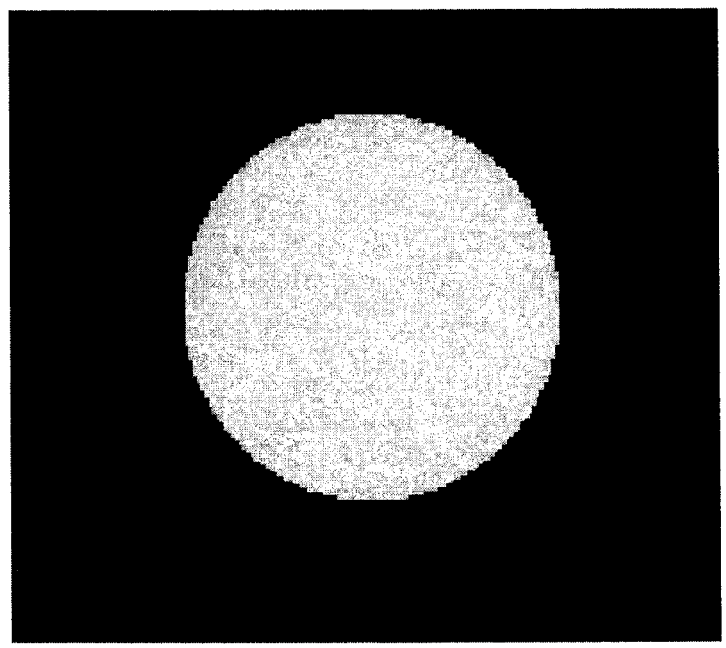
FIG. 22 shows a computer simulation of a $T_1$ weighted image of the tumour and surrounding interstitial fluid as shown in FIGS. 17, 18 and 19 obtained with the tumour positioned located at the iso-center and using an MRI machine with a modified z-gradient coil programmed to generate a ΔB magnetic field that is substantially uniform across the imaging region.

FIG. 22 shows a simulated DREMR image where the sample is at iso-center and a modified gradient coil as shown in FIGS. 10 to 14 has been used to generate a substantially uniform ΔB auxiliary magnetic field at all points across the imaging region. The ΔB auxiliary magnetic field of 40 mT is used to produce a first $T_1$ weighted image. The ΔB auxiliary magnetic field is then reversed at −40 mT to produce a second $T_1$ weighted image. Subtraction of the first and second $T_1$ weighted images produces the DREMR image. The image shown in FIG. 22 benefits from a lack of shading across the tumour, thereby increasing contrast over the background interstitial fluid. Furthermore, this image quality can be produced independent of the positioning of the target sample, including positioning at the iso-center.

Figure 23:
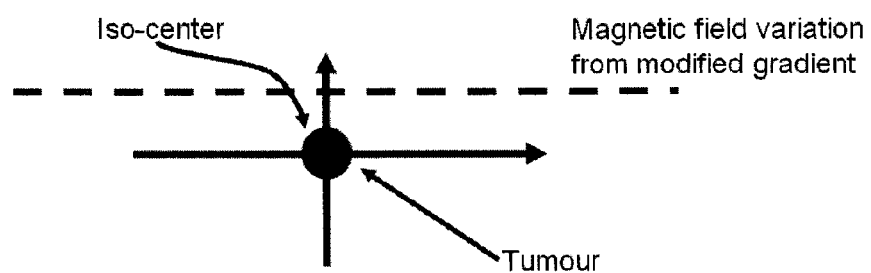
FIG. 23 shows the ΔB magnetic field and tumour position used to obtain the image shown in FIG. 22.

FIG. 23 shows the setup for FIG. 22. The tumour is placed at the iso-center similar to the setup for FIG. 18, but because the modified gradient coil generates a substantially uniform ΔB auxiliary magnetic field across the target sample an improved image is obtained in FIG. 22 compared to FIGS. 17, 18 and 20.

The software application used to drive the electromagnetic ΔB insert, the gradient coil, or the modified gradient coil may run as a stand-alone application or may be incorporated into other available applications to provide enhanced functionality to those applications. The software application may comprise program modules including routines, programs, object components, data structures etc. and may be embodied as computer readable program code stored on a computer readable medium. The computer readable medium is any data storage device that can store data, which can thereafter be read by a computer system. Examples of computer readable media include for example read-only memory, random-access memory, CD-ROMs, magnetic tape and optical data storage devices. The computer readable program code can also be distributed over a network including coupled computer systems so that the computer readable program code is stored and executed in a distributed fashion.

In one particular embodiment, the method and system take advantage of the change in longitudinal relaxivity vs. field strength, i.e. the relaxivity slope, to generate selective image contrast occurring when a contrast agent binds to a given target molecule. In other embodiments, variations other than the slope may be examined.

The system and method have been described in respect of embodiments relating to $T_1$ relaxation times and $T_1$ contrast agents. In other embodiments, the system and method may be adapted to produce image contrast related to the magnetic field dependence of $T_2$ contrast agents.

The system and method described herein is readily applicable to any type of MRI machine, for example bore or gap-type MRI machines.

The polarizing magnetic field $B_0$ generated by the MRI machine may be of any desired strength, but will typically be greater than 0.2 T.

The system and method have been described with respect to embodiments where an auxiliary magnetic field is provided by either an insert or a gradient coil. It will be recognized that various MRI pulse sequences may be combined with gradient pulses during the relaxation portion of the pulse sequence to produce image contrast. Any number of gradient coils may be used to generate the ΔB magnetic field during the relaxation portion of the pulse sequence, for example one gradient coil may be used alone or multiple gradient coils may be used in combination. Any conventional gradient coil can be reprogrammed or modified in accordance with the system and method described herein, including for example flat or planar gradient coils.

When offsetting a target from the iso-center, the target may be offset along one or more of the x, y and z axis of a Cartesian coordinate system.

The above-described embodiments are intended to be examples and alterations and modifications may be effected thereto, by those of skill in the art, without departing from the scope of the invention which is defined by the claims appended hereto.

REFERENCES

1. Weissleder R, Mahmood U. Molecular imaging. Radiology 2001; 219(2):316-333.
2. Nahrendorf M, Sosnovik D E, Weissleder R. M R-optical imaging of cardiovascular molecular targets. Basic research in cardiology 2008; 103(2):87-94.
3. Hendrick R E, Haacke E M. Basic physics of M R contrast agents and maximization of image contrast. J Magn Reson Imaging 1993; 3(1):137-148.
4. Wood M L, Hardy P A. Proton relaxation enhancement. J Magn Reson Imaging 1993; 3(1):149-156.
5. Caravan P, Cloutier N J, Greenfield M T, McDermid S A, Dunham S U, Bulte J W, Amedio J C, Jr., Looby R J, Supkowski R M, Horrocks W D, Jr., McMurry T J, Lauffer R B. The interaction of MS-325 with human serum albumin and its effect on proton relaxation rates. Journal of the American Chemical Society 2002; 124(12): 3152-3162.
6. Henrotte V, Vander Elst L, Laurent S, Muller R N. Comprehensive investigation of the non-covalent binding of MRI contrast agents with human serum albumin. J Biol Inorg Chem 2007; 12(6):929-937.
7. Eldredge H B, Spiller M, Chasse J M, Greenwood M T, Caravan P. Species dependence on plasma protein binding and relaxivity of the gadolinium-based MRI contrast agent MS-325. Investigative radiology 2006; 41(3):229-243.
8. Nahrendorf M, Sosnovik D, Chen J W, Panizzi P, Figueiredo J L, Aikawa E, Libby P, Swirski F K, Weissleder R. Activatable magnetic resonance imaging agent reports myeloperoxidase activity in healing infarcts and noninvasively detects the antiinflammatory effects of atorvastatin on ischemia-reperfusion injury. Circulation 2008; 117(9):1153-1160.
9. Overoye-Chan K, Koerner S, Looby R J, Kolodziej A F, Zech S G, Deng Q, Chasse J M, McMurry T J, Caravan P. EP-2104R: a fibrin-specific gadolinium-Based MRI contrast agent for detection of thrombus. Journal of the American Chemical Society 2008; 130(18):6025-6039.
10. Alford J K. Delta relaxation enhanced M R (dreMR): Theory of T1-slope weighted contrast. ISMRM. Toronto, Canada; 2008.
11. Carlson J W, Goldhaber D M, Brito A, Kaufman L. M R relaxometry imaging. Work in progress. Radiology 1992; 184(3):635-639.
12. Ungersma S E, Matter N I, Hardy J W, Venook R D, Macovski A, Conolly S M, Scott G C. Magnetic resonance imaging with T1 dispersion contrast. Magn Reson Med 2006; 55(6):1362-1371.
13. Bottomley P A, Foster T H, Argersinger R E, Pfeifer L M. A review of normal tissue hydrogen NMR relaxation times and relaxation mechanisms from 1-100 MHz: dependence on tissue type, NMR frequency, temperature, species, excision, and age. Med Phys 1984; 11(4):425-448.
14. Henriksen O, de Certaines J D, Spisni A, Cortsen M, Muller R N, Ring P B. In vivo field dependence of proton relaxation times in human brain, liver and skeletal muscle: a multicenter study. Magn Reson Imaging 1993; 11(6):851-856.

15. Zhou X, Caravan P, Clarkson R B, Westlund P O. On the philosophy of optimizing contrast agents. An analysis of 1H NMRD profiles and ESR lineshapes of the Gd(III) complex MS-325+HSA. J Magn Reson 2004; 167(1):147-160.
16. Gilbert K M, Handler W B, Scholl T J, Odegaard J W, Chronik B A. Design of field-cycled magnetic resonance systems for small animal imaging. Phys Med Biol 2006; 51(11):2825-2841.
17. Matter N I, Scott G C, Grafendorfer T, Macovski A, Conolly S M. Rapid polarizing field cycling in magnetic resonance imaging. IEEE Trans Med Imaging 2006; 25(1):84-93.
18. Lurie D J, Foster M A, Yeung D, Hutchison J M. Design, construction and use of a large-sample field-cycled PEDRI imager. Phys Med Biol 1998; 43(7):1877-1886.
19. Alford J. From static to dynamic: Construction of an actively shielded $B_0$ coil for field-cycled imaging with clinical M R platforms. ISMRM. Toronto, Canada; 2008.

Documents cited in this specification are herein incorporated by reference.

What is claimed is:

1. A magnetic resonance imaging (MRI) method comprising:
   acquiring image data of a target having a concentration of contrast agent using an MRI machine, said contrast agent binding to the target and demonstrating a magnetic field-dependent variation in one or more MRI properties, said acquiring comprising:
   shifting the strength of a polarizing magnetic field of said MRI machine in one of a positive direction and a negative direction to expose the target to one of an increased polarizing magnetic field and a decreased polarizing magnetic field, and during shifting of the polarizing magnetic field in the positive direction, generating a substantially uniform positive magnetic field, and during shifting of the polarizing magnetic field in the negative direction, generating a substantially uniform negative magnetic field,
   returning the polarizing magnetic field to its static strength and then acquiring image data of the target,
   shifting the strength of the polarizing magnetic field of said MRI machine in the other of the positive direction and the negative direction to expose the target to the other of the increased polarizing magnetic field and the decreased polarizing magnetic field, and during shifting of the polarizing magnetic field in the positive direction, generating a substantially uniform positive magnetic field, and during shifting of the polarizing magnetic field in the negative direction, generating a substantially uniform negative magnetic field, and
   returning the polarizing magnetic field to its static strength and then acquiring image data of the target; and
   fitting the acquired image data to a signal model to yield enhanced contrast image data.

2. The method of claim 1, wherein the strength of the polarizing magnetic field is shifted in the positive and negative directions by substantially the same amount.

3. The method of claim 2, wherein the polarizing magnetic field is shifted using at least one gradient coil of the MRI machine.

4. The method of claim 1, further comprising offsetting the target from an iso-center of the MRI machine.

5. The method of claim 1, wherein the MRI pulse sequence is a spin-echo pulse sequence.

6. An MRI machine comprising:
   a housing configured to accommodate a target having a concentration of a contrast agent, said contrast agent binding to the target, concentrating in the target, and demonstrating magnetic field-dependent variation in MRI relaxation properties;
   a polarizing electromagnet disposable in relation to said housing and configured to generate a polarizing magnetic field;
   pulse generating coils configured to generate pulses in an MRI pulse sequence to scan the target in the presence of said polarizing magnetic field;
   gradient coils configured to encode acquired MRI signals, wherein said gradient coils are further configured to:
     shift the strength of the polarizing magnetic field generated by the polarizing electromagnet of said MRI machine in one of a positive direction and a negative direction to expose the target to one of an increased polarizing magnetic field and a decreased polarizing magnetic field prior to scanning in the presence of said polarizing magnetic field; and
     shift the strength of the polarizing magnetic field generated by the polarizing electromagnet of said MRI machine in the other of the positive direction and the negative direction to expose the target to the other of the increased polarizing magnetic field and the decreased polarizing magnetic field prior to scanning in the presence of said polarizing magnetic field;
     during shifting of the polarizing magnetic field in the positive direction, generate a substantially uniform positive magnetic field, and during shifting of the polarizing magnetic field in the negative direction, generate a substantially uniform negative magnetic field; and
   a computing device configured to fit acquired image data to a signal model to yield contrast image data of the target.

7. The MRI machine of claim 6, wherein the MRI pulse sequence is a spin-echo pulse sequence.

* * * * *